US009069917B2

(12) United States Patent
Shimanuki

(10) Patent No.: US 9,069,917 B2
(45) Date of Patent: Jun. 30, 2015

(54) COMPONENT FRACTURE EVALUATION DEVICE, COMPONENT FRACTURE EVALUATION METHOD AND COMPUTER PROGRAM

(71) Applicant: NIPPON STEEL & SUMITOMO METAL CORPORATION, Tokyo (JP)

(72) Inventor: Hiroshi Shimanuki, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days.

(21) Appl. No.: 14/344,220

(22) PCT Filed: May 13, 2013

(86) PCT No.: PCT/JP2013/063286
§ 371 (c)(1),
(2) Date: Mar. 11, 2014

(87) PCT Pub. No.: WO2013/179877
PCT Pub. Date: Dec. 5, 2013

(65) Prior Publication Data
US 2014/0350904 A1 Nov. 27, 2014

(30) Foreign Application Priority Data

May 29, 2012 (JP) ................................. 2012-122295

(51) Int. Cl.
*G06G 7/48* (2006.01)
*G06F 17/50* (2006.01)
(Continued)

(52) U.S. Cl.
CPC ........ *G06F 17/5009* (2013.01); *G06F 17/5018* (2013.01); *G01N 3/32* (2013.01); *G01N 2203/0218* (2013.01); *G06F 2217/76* (2013.01); *G01M 13/00* (2013.01)

(58) Field of Classification Search
CPC ............ G06F 17/5009; G06F 17/5018; G06F 2217/76; G01N 3/32; G01N 2203/0218; G01M 13/00
USPC ....................... 703/2, 6; 702/34, 181; 82/1.11; 148/320; 428/596; 123/456
See application file for complete search history.

(56) References Cited

U.S. PATENT DOCUMENTS

2003/0089428 A1* 5/2003 Murakami et al. ............. 148/320
2004/0016326 A1* 1/2004 Liu et al. ........................ 82/1.11
(Continued)

FOREIGN PATENT DOCUMENTS

JP    63-194279 A     8/1988
JP    2010-256351 A   11/2010
JP    2012-73059 A    4/2012

OTHER PUBLICATIONS

Allazadeh, "The effect of cooling rate on the microstructure configuration of continuously cast steel slabs", University of Pittsburgh 2009.*

(Continued)

*Primary Examiner* — Kandasamy Thangavelu
(74) *Attorney, Agent, or Firm* — Birch, Stewart, Kolasch & Birch, LLP

(57) ABSTRACT

A probability in which a stress amplitude $\sigma_p$ of an operating stress exceeds a stress amplitude $\sigma_w$ of a fatigue strength (a fatigue strength excess probability $p_{V0}$ of a virtual cell) at each virtual cell in which a region of a machine component is equally divided so that one inclusion is contained therein and having a virtual unit volume $V_0$ is derived on an assumption that a distribution function of an inclusion size $\sqrt{area}$ follows a generalized Pareto distribution. Then a probability in which the stress amplitude $\sigma_p$ of the operating stress exceeds the stress amplitude $\sigma_w$ of the fatigue strength (a fatigue strength excess probability $p_{fV}$ of the machine component) in at least one virtual cell is derived from the fatigue strength excess probability $p_{V0}$.

11 Claims, 11 Drawing Sheets

(51) Int. Cl.
*G01N 3/32* (2006.01)
*G01M 13/00* (2006.01)

(56) References Cited

U.S. PATENT DOCUMENTS

| | | | |
|---|---|---|---|
| 2010/0055490 A1* | 3/2010 | Sugihashi et al. | 428/596 |
| 2011/0005493 A1* | 1/2011 | Hirano et al. | 123/456 |
| 2011/0137575 A1* | 6/2011 | Koul | 702/34 |
| 2012/0065934 A1* | 3/2012 | Shimanuki et al. | 702/181 |
| 2013/0060536 A1* | 3/2013 | Sukup et al. | 703/2 |

OTHER PUBLICATIONS

Shi et al., "Computer simulation of the estimation of the maximum inclusion size in clean steels by the Generalized Pareto Distribution method", Acta Materialia Inc., 2001.*
Shi et al., "Application of the Generalized Pareto Distribution to the estimation of the size of the maximum inclusion in clean steels", Acta Materialia Inc., 1999.*
Wormsen, A., "A Fatigue Assessment Methodology for Notched Components Containing Defects", Norwegian University of Science and Technology, Oct. 2007.*
Anderson, C.W., et al. "The precision of methods using the statistics of extremes for the estimation of the maximum size of inclusions in clean steels," Acta Mater., 2000, vol. 48, No. 17, pp. 4235-4246.
Hu, Chao, et al. "Locally enhanced Voronoi cell finite element model (LE-VCFEM) for simulating evolving fracture in ductile microstructures containing inclusions," International Journal for Numerical Methods in Engineering, 2008, vol. 76, No. 12, pp. 1955-1992.
International Search Report issued in PCT/JP2013/063286 mailed Jul. 2, 2013.
Murakami, Yukitaka. "Evaluation of Inclusion of Medium Carbon Steel by Extreme Value Statistics and Predicated Actual Example of Fatigue Limit Lower Limit Value," Metal Fatigue; Effects of small defects and inclusions, OD ed. 1st ed., Yokendo, Dec. 25, 2008, pp. 245-250, Chapter A6.
Shimanuki, Hiroshi. "Effect of Inclusion Size on Giga-Cycle Fatigue Properties of SUJ2," Materials and Processes, 2010, vol. 23, p. 688, Fig. 2.
Written Opinion of the International Searching Authority issued in PCT/JP2013/063286 mailed Jul. 2, 2013.
Zhang, J.M., et al. "Estimation of maximum inclusion size and fatigue strength in high-strength ADF1 steel," Materials Science and Engineering a Structural Materials: Properties, Microstructure and Processing, 2005, vol. A394, No. 1/2, pp. 126-131.
Kazuaki Matsumoto et al.; "Effect of Inclusion on Rotating Bending Fatigue Strength of Carburized and Shot-Peened Steels for Gear Use" Proceedings of the Japan Society of Mechanical Engineers Conference on Material Mechanics; No. 900-86; 1990; pp. 275-277.
Craig P Przybyla et al. "Simulated microstructure-sensitive extreme value probabilities for high cycle fatigue of duplex Ti6Al4V", International Journal of Plasticity 27 (2011) pp. 1871-1895.
European Search Report issued in PCT/JP2013/063286 mailed Oct. 23, 2014.
Owolabi G M et al. "A Micromechanics-Based Fatigue Damage Process Zone", Procedia Engineering 10 (2011) pp. 496-505.
International Preliminary Report on Patentability (form PCT/IB/373) dated Dec. 2, 2014, with English translation of Written Opinion of the International Searching Authority (form PCT/ISA/237) dated Jul. 2, 2013, for International Appl. No. PCT/JP2013/063286.

* cited by examiner

NUMBER OF INCLUSIONS: $N_0 = N_u + \alpha$  NUMBER OF INCLUSIONS: 1
VOLUME: $V_s$  VOLUME: $V_0$

COMPONENT FRACTURE EVALUATION DEVICE, COMPONENT FRACTURE EVALUATION METHOD AND COMPUTER PROGRAM

TECHNICAL FIELD

The present invention relates to a component fracture evaluation device, a component fracture evaluation method and a computer program, and particularly, it is preferably used to evaluate fracture performance in a machine component.

BACKGROUND ART

In a high-tensile steel machine component receiving high-cycle load, it is necessary to reduce a risk of breakage troubles of components caused by an internal fatigue fracture starting from internal defects such as inclusions. It is conceivable that a size of the inclusion to be the starting point and an existence probability of the inclusion at a high-stress portion have large influence on the internal fatigue fracture. Conventionally, a method forecasting a fatigue limit starting from the inclusion has been formulated, and it is possible to estimate the fatigue limit by an estimated formula as stated above under a uniform stress (refer to Non-Patent Literature 1).

However, there is no effective method to evaluate the fracture performance as the machine component such as a spring having a complicated stress distribution such as effects of a shot peening and a shear stress. Accordingly, the present situation is that a fatigue design is performed based on an existing fatigue design diagram and so on based on an actual performance of materials.

CITATION LIST

Patent Literature

Patent Literature 1: Japanese Laid-open Patent Publication No. 2010-256351
Patent Literature 2: Japanese Laid-open Patent Publication No. S63-194279

Non Patent Literature

Non Patent Literature 1: "Metal Fatigue; Effects of small defects and inclusions", MURAKAMI Yukitaka, Yokendo, Dec. 25, 2008, OD edition first edition
Non Patent Literature 2: SHIMANUKI H.; Effect of Inclusion Size on Giga-Cycle Fatigue Properties of SUJ2, CAMP-ISIJ, (2010), p 688.

SUMMARY OF INVENTION

Technical Problem

According to an art described in Non-Patent Literature 1, it is possible to perform a fatigue design of a machine component in consideration of a volume effect affecting on a fatigue fracture phenomenon under a uniform stress by a formula finding a fatigue strength of the machine component and a formulation of a maximum inclusion size and a maximum inclusion distribution by an extreme value statistical processing. However, it is impossible to perform the fatigue design of the machine component in consideration of both influences of the volume effect (the size of the inclusion and a distribution of density) and a distribution of stress inside the machine component according to the art described in Non-Patent Literature 1.

Besides, it is necessary to create a P-S-N curve by performing a number of fatigue tests and to create a Weibull plot relating to the fatigue strength of the material to find variation of the fracture strength of the material by using an art described in Patent Literature 1. Besides, according to the art described in Patent Literature 1, it is impossible to consider a difference of material characteristics (distribution of inclusions) by each position of the machine component (in addition to the variation of the fatigue strength of the material).

The present invention is made in consideration of the above-described problems and has an object to make it possible to evaluate fracture performance of a machine component in consideration of distribution of inclusions existing inside the machine component.

Solution to Problem

A component fracture evaluation method according to the present invention is a component fracture evaluation method evaluating fracture performance of a machine component, and includes: an inclusion extracting process of extracting inclusions contained in a sample from the sample made up of the same kind of material as a material constituting the machine component; a threshold value excess number of inclusions deriving process deriving a threshold value excess number of inclusions being the number of inclusions whose inclusion size exceeds a threshold value among the inclusions contained in the sample based on the inclusion size being a size of the inclusion extracted by the inclusion extracting process; a coefficient deriving process deriving coefficients of a generalized Pareto distribution based on the inclusion size of the inclusion extracted by the inclusion extracting process, the threshold value excess number of inclusions by the threshold value excess number of inclusions deriving process, and the threshold value on an assumption that a distribution function of the inclusion size of the inclusion extracted by the inclusion extracting process follows the generalized Pareto distribution; a virtual inclusion ratio deriving process deriving a virtual inclusion ratio being a ratio between the threshold value excess number of inclusions being the number of inclusions whose inclusion size exceeds the threshold value among the inclusions contained in the sample and a zero excess number of inclusions being the number of inclusions whose inclusion size exceeds "0" (zero) among the inclusions contained in the sample; and a virtual unit volume deriving process deriving a virtual unit volume being a volume of a virtual cell when the machine component is equally divided by plural virtual cells each containing one inclusion based on the threshold value excess number of inclusions, the virtual inclusion ratio, and a volume of the sample, wherein an index evaluating the fracture performance of the machine component is derived by a unit of the virtual cell having the virtual unit volume derived by the virtual unit volume deriving process, and the fracture performance of the machine component is evaluated by using the derived index.

A component fracture evaluation device according to the present invention is a component fracture evaluation device evaluating fracture performance of a machine component, and includes: a threshold value excess number of inclusions deriving unit deriving a threshold value excess number of inclusions being the number of inclusions whose inclusion size exceeds a threshold value among the inclusions contained in a sample based on the inclusion size being a size of the inclusion extracted from the sample made up of the same kind of material as a material constituting the machine component; a coefficient deriving unit deriving coefficients of a generalized Pareto distribution based on the inclusion size of the extracted inclusion, the threshold value excess number of inclusions, and the threshold value on an assumption that a distribution function of the inclusion size of the extracted inclusion follows the generalized Pareto distribution; a virtual inclusion ratio deriving unit deriving a virtual inclusion ratio being a ratio between the threshold value excess number of inclusions being the number of inclusions whose inclusion size exceeds the threshold value among the inclusions contained in the sample and a zero excess number of inclusions being the number of inclusions whose inclusion size exceeds "0" (zero) among the inclusions contained in the sample; and a virtual unit volume deriving unit deriving a virtual unit volume being a volume of a virtual cell when the machine component is equally divided by plural virtual cells each containing one inclusion based on the threshold value excess number of inclusions, the virtual inclusion ratio, and a volume of the sample, wherein an index evaluating the fracture performance of the machine component by a unit of the virtual cell having the virtual unit volume derived by the virtual unit volume deriving unit is derived, and the fracture performance of the machine component is evaluated by using the derived index.

A computer program according to the present invention for causes a computer to execute an evaluation of fracture performance of a machine component, the computer program causes the computer to execute: a threshold value excess number of inclusions deriving process deriving a threshold value excess number of inclusions being the number of inclusions whose inclusion size exceeds a threshold value among the inclusions contained in a sample based on the inclusion size being a size of the inclusion extracted from the sample made up of the same kind of material as a material constituting the machine component; a coefficient deriving process deriving coefficients of a generalized Pareto distribution based on the inclusion size of the extracted inclusion, the threshold value excess number of inclusions, and the threshold value on an assumption that a distribution function of the inclusion size of the extracted inclusion follows the generalized Pareto distribution; a virtual inclusion ratio deriving process deriving a virtual inclusion ratio being a ratio between the threshold value excess number of inclusions being the number of inclusions whose inclusion size exceeds the threshold value among the inclusions contained in the sample and a zero excess number of inclusions being the number of inclusions whose inclusion size exceeds "0" (zero) among the inclusions contained in the sample; and a virtual unit volume deriving process deriving a virtual unit volume being a volume of a virtual cell when the machine component is equally divided by plural virtual cells each containing one inclusion based on the threshold value excess number of inclusions, the virtual inclusion ratio, and a volume of the sample, wherein an index evaluating the fracture performance of the machine component by a unit of the virtual cell having the virtual unit volume derived by the virtual unit volume deriving process is derived, and the fracture performance of the machine component is evaluated by using the derived index.

Advantageous Effects of Invention

According to the present invention, a machine component is equally divided by plural virtual cells each containing one inclusion on an assumption that a distribution function of an inclusion size follows a generalized Pareto distribution. An index to evaluate fracture performance of the machine component by a unit of each virtual cell is derived, and the fracture performance of the machine component is evaluated by using the derived index. Accordingly, it is possible to evaluate the fracture performance of the machine component in consideration of the distribution of the inclusions existing inside the machine component.

DESCRIPTION OF EMBODIMENTS

Figure 1:
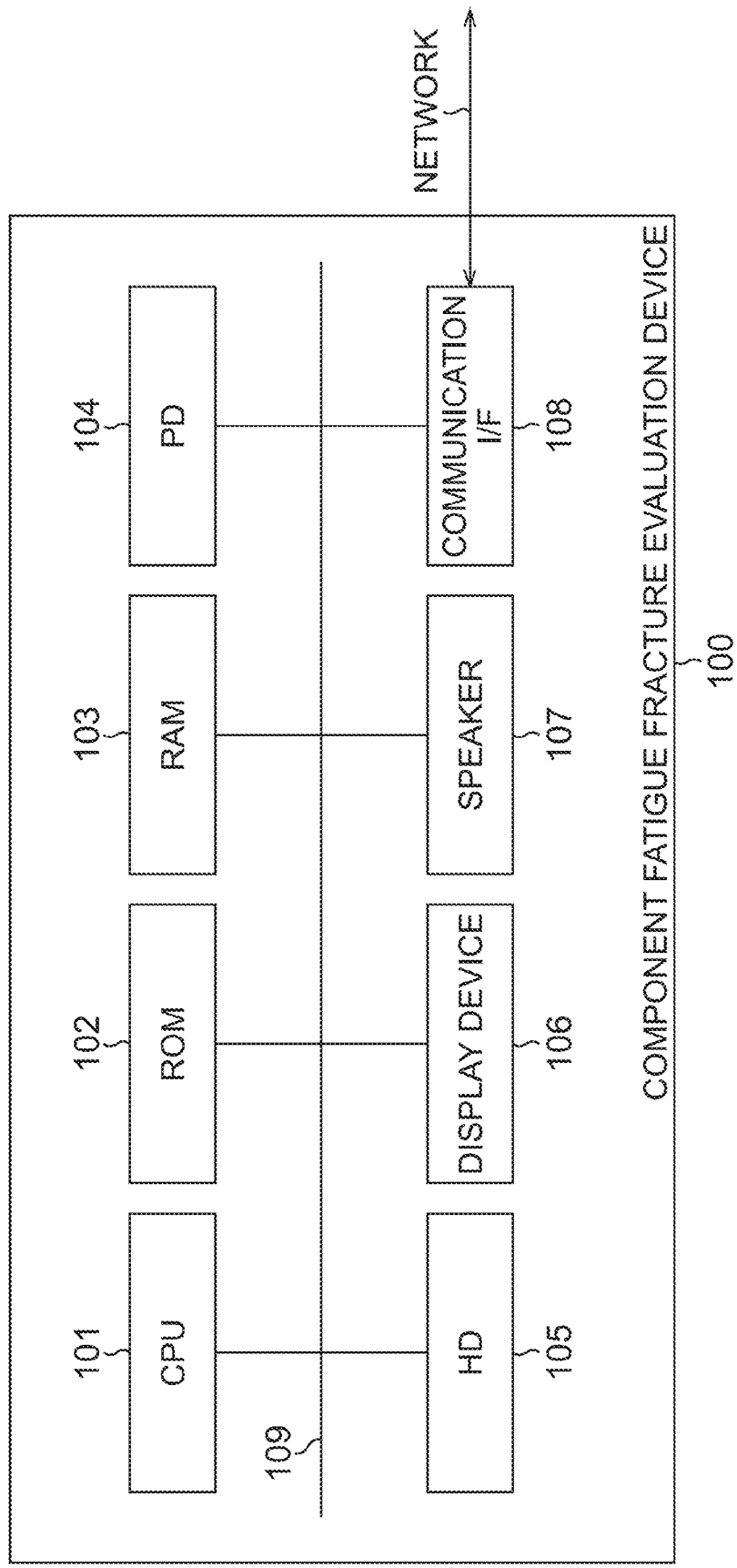
FIG. 1 is a view illustrating an example of a hardware configuration of a component fatigue fracture evaluation device.

A background in which embodiments of the present invention are brought to mind is described before the embodiments of the present invention are described.

It is known that so-called a fatigue limit is not seen and a fatigue strength gradually deteriorates even at a long lifetime region as for an internal fatigue fracture starting from inclusions contained in a high-tensile steel. However, an inclination thereof is extremely small, and the present inventors experimentally verify that a lifetime differs for 1000 times or more even between inclusions having approximately the same size. Namely, it can be seen that it is rational to make a fatigue design of a material as stated above not by the lifetime but by the fatigue strength (refer to Non-Patent Literature 2).

Besides, when a high stress amplitude incurring internal fatigue is applied on the high-tensile steel, a stress intensity factor becomes rapidly large once a crack occurs. Accordingly, a crack growth rate is fast and the cracks rapidly grow to incur the fatigue fracture in the high-tensile steel. Therefore, when a machine component whose cross section is small such as a spring is manufactured by the high-tensile steel, a fracture lifetime of the machine component is almost controlled by an occurrence lifetime of the fatigue cracks.

In recent years, sizes and the number of inclusions existing inside the high-tensile steel become small to prevent the internal fatigue fracture. Accordingly, it is difficult to detect the inclusions in the material as stated above. However, it is possible to measure a degree of existence of inclusions each having a size of a threshold value or more in a predetermined volume of a certain material by using methods such as a slime extraction method in which only inclusions are extracted by melting a material having a certain degree of volume in an electrolytic solution and an acid melding method. However, a minimum limit size of the inclusions capable of being collected depends on roughness of a filter of a device in the methods as stated above, and it is impossible to extract all inclusions. Fortunately, the internal fatigue fracture is not a problem in a small inclusion. Accordingly, it is effective to evaluate the fracture of the machine component by using only a distribution of large inclusions which contribute to the internal fatigue.

Besides, there are possibilities in which strength, internal stress, and so on largely vary depending on positions because processes at a surface layer and an inside are different, and therefore, it is necessary to evaluate the fatigue fracture in consideration of the above.

The present inventors found a method to quantitatively figure out a probability exceeding the fatigue strength of the machine component when a stress state (mean stress, repetitive stress) is applied as described below based on information and conditions as stated above. It is possible to obtain a principal to determine an effective measure to prevent the fatigue fracture by using this method.

Hereinafter, an embodiment of the present invention is described with reference to the drawings.

<Hardware Configuration of Component (Machine Component) Fatigue Fracture Evaluation Device>

FIG. 1 is a view illustrating an example of a hardware configuration of a component fatigue fracture evaluation device 100. The component fatigue fracture evaluation device 100 is one to evaluate fracture performance of a machine component.

As illustrated in FIG. 1, the component fatigue fracture evaluation device 100 includes a CPU (Central Processing Unit) 101, a ROM (Read Only Memory) 102, a RAM (Random Access Memory) 103, a PD (Pointing Device) 104, an HD (Hard Disk) 105, a display device 106, a speaker 107, a communication I/F (Interface) 108, and a system bus 109.

The CPU 101 is one totally controlling operations at the component fatigue fracture evaluation device 100, and controls respective configuration units (102 to 108) of the component fatigue fracture evaluation device 100 via the system bus 109.

The ROM 102 stores BIOS (Basic Input/Output System) and operating system program (OS) being control programs of the CPU 101, and programs and so on necessary for the CPU 101 to execute the later-described processes.

The RAM 103 functions as a main memory, a work area, and so on of the CPU 101. The CPU 101 loads necessary computer programs and so on from the ROM 102, necessary information and so on from the HD 105 to the RAM 103 when the processes are executed, and enables various operations by executing the computer programs and so on, the processes of the information and so on.

The PD 104 is made up of, for example, a mouse, a keyboard, and so on, and constitutes an operation input unit enables an operator to perform an operation input for the component fatigue fracture evaluation device 100 according to need.

The HD 105 constitutes a storage unit storing various information, data, files and so on.

The display device 106 constitutes a display unit displaying various information and images based on the control of the CPU 101.

The speaker 107 constitutes a sound output unit outputting sounds relating to various information based on the control of the CPU 101.

The communication I/F 108 performs communication of various information and so on with external devices via a network based on the control of the CPU 101.

The system bus 109 is a bus to connect the CPU 101, the ROM 102, the RAM 103, the PD 104, the HD 105, the display device 106, the speaker 107 and the communication I/F 108 so as to be able to communicate with each other.

<Component Fatigue Fracture Evaluation Device>

Figure 2:
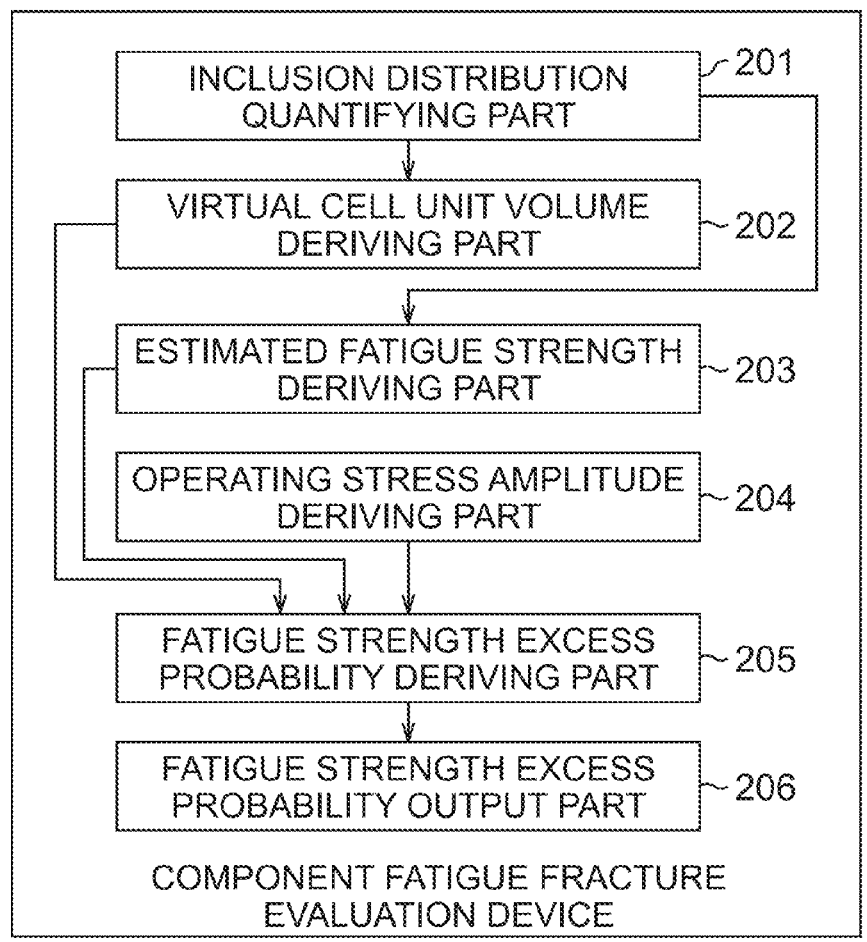
FIG. 2 is a view illustrating an example of a functional configuration of the component fatigue fracture evaluation device.

FIG. 2 is a view illustrating an example of a functional configuration of the component fatigue fracture evaluation device 100. The component fatigue fracture evaluation device 100 of the present embodiment assumes the number of inclusions existing in one machine component such as a spring based on an investigation result of distribution of inclusions of a material constituting the machine component, determines a probability whether or not each of the inclusions exceeds a fatigue strength relative to a stress state (the mean stress and the repetitive stress) where each one of the inclusions exist, and calculates a fatigue strength excess probability as a whole of the machine component by generalizing the results thereof.

In FIG. 2, the component fatigue fracture evaluation device 100 includes an inclusion distribution quantifying part 201, a virtual cell unit volume deriving part 202, an estimated fatigue strength deriving part 203, an operating stress amplitude deriving part 204, a fatigue strength excess probability deriving part 205, and a fatigue strength excess probability output part 206.

<Inclusion Distribution Quantifying Part 201>

At first, sizes of respective inclusions (inclusion size $\sqrt{area}$ [μm]) contained in a sample made up of the same kind of material as a material constituting a machine component to be an investigation object of the fatigue strength excess probability are measured (a volume of the sample is set to be $V_s$ [mm$^3$]). Here, the inclusion size $\sqrt{area}$ is one so-called a "root area", and is a value in which a square root ($\sqrt{\ }$) of a projected area (a cross-sectional area of the inclusion) is taken when a shape of the inclusion is projected on a plane. However, it is actually difficult to accurately find the area as stated above, and therefore, it is not exactly necessary to do as stated above. For example, the shape of the inclusion is approximated to a simple figure (shape) such as a quadrangle and an ellipse, and the projected area of the inclusion (the cross-sectional area of the inclusion) is estimated to be found from a representative size of the figure, and the square root of the area may be used as the inclusion size $\sqrt{\text{area}}$. When the shape of the inclusion is approximated to the ellipse as a concrete example, a value in which the square root of a product of a major axis and a minor axis is taken or a value in which the square root of a product of the major axis, the minor axis, and $\pi$ is taken is simply set to be an estimated value (the inclusion size $\sqrt{\text{area}}$) of the projected area (the cross-sectional area of the inclusion).

Note that in the present description, $\sqrt{X}$ represents $X^{1/2}$ (a ½-th power of X), and for example, $\sqrt{\text{area}_{max}}$ represents $\text{area}_{max}^{1/2}$.

The extraction of the inclusion as stated above can be performed by using, for example, a slime method. The slime method is a method in which a sample is electrolyzed in a ferrous solution, an electrolyzed slime is collected in a mesh sampling bag, residue other than the inclusion made up of nonferrous metal is removed by an elutriation work, the residue left in the sampling bag is transferred to a magnetic plate to further remove the residue, and thereafter, a sieving separation work is performed.

Note that the slime method is a publicly-known art as described in Patent Literature 2 and so on, and therefore, a detailed description thereof is not given here. Besides, here, a case when the number of inclusions is measured by using the slime method is exemplified to be described. However, the inclusion extraction process is not limited to the slime method. For example, the inclusions contained in the sample may be extracted by using the other methods such as an acid melting method and a microscopic method, to measure the respective inclusion sizes $\sqrt{\text{area}}$.

The inclusion distribution quantifying part 201 inputs and stores each information of the sizes of the inclusions (the inclusion size $\sqrt{\text{area}}$) extracted by the slime method and so on among the inclusions contained in the sample based on the operation of the operator, the communication with the external devices, and so on. Note that in the following description, the information of the inclusion size $\sqrt{\text{area}}$ obtained as stated above is called as an "actual measurement data" according to need.

In the present embodiment, a probability distribution of the inclusion size $\sqrt{\text{area}}$ is represented by a conditional probability P of an inclusion whose inclusion size $\sqrt{\text{area}}$ exceeds "x" from among the inclusions whose inclusion size $\sqrt{\text{area}}$ exceeds a threshold value u. Then, a density function p of the inclusion size $\sqrt{\text{area}}$ is approximately represented by the following formula (1) or formula (2).

$$p(x) = \{1 + \xi(x-u)/\sigma\}^{-1/\xi - 1} \quad (1)$$

where $1 + \xi(x-u)/\sigma > 0$, $\xi \neq 0$ $$p(x) = \exp(-(x-u)/\sigma) \quad (2)$$

where it is a singular solution (exponential distribution) when $\xi = 0$

In the formula (1), "$\xi$", "$\sigma$" are coefficients [−], "u" is the threshold value of the inclusion size [μm], $x = x_1, x_2, \ldots, x_{N_u}$, is the size of the inclusion (the inclusion size $\sqrt{\text{area}}$) [μm] which is the threshold value u or more.

Here, when $\xi > 0$, the formula (1) is the density function of the Pareto distribution, and when $\xi < 0$, the formula (1) is the density function of a beta distribution. Besides, the formula (2) is the exponential distribution. As stated above, the names of the distribution function change depending on the value of the coefficient $\xi$, but these are generically named as the density function of a generalized Pareto distribution. As stated above, in the present embodiment, the distribution function of the inclusion size $\sqrt{\text{area}}$ follows the generalized Pareto distribution.

In the slime method, it is impossible to extract all of the inclusions contained in the sample, and the inclusions whose inclusion sizes $\sqrt{\text{area}}$ are small cannot be extracted. Accordingly, the inclusion distribution quantifying part 201 derives a threshold value excess number of inclusions $N_u$ being the number of inclusions each of whose inclusion sizes $\sqrt{\text{area}}$ exceeds the threshold value u from the actual measurement data. The inclusion distribution quantifying part 201 determines the threshold value u based on, for example, an average excess plot obtained by plotting a value of the following formula (3), or a median excess plot obtained by plotting a value of the following formula (4), and it becomes possible to find the threshold value excess number of inclusions $N_u$. At this time, the inclusion distribution quantifying part 201 displays the average exceed plot or the median exceed plot on the display device 106, determines the threshold value u based on the operation of the PD 104 by the operator for the displayed result, and is able to derive the number of the inclusions exceeding the threshold value u as the threshold value excess number of inclusions $N_u$.

[Numerical Formula 1]

$$\left\{\left(u, \frac{1}{N_u}\sum_{i=1}^{N_u}(x(i)-u)\right) : u < x_{max}\right\} \quad (3)$$

$$\{(u, \text{median}_{1 \leq i \leq N_u}\{x(i) - u\}) : u < x_{max}\} \quad (4)$$

In the formula (3) and the formula (4), "i" is a variable [−] identifying the inclusion, and "$x_{max}$" is a maximum value [μm] of the inclusion size $\sqrt{\text{area}}$ contained in the actual measurement data. Here, there is no need to exactly define the threshold value u of the inclusion size $\sqrt{\text{area}}$, and a size at a degree assumed to contribute to a fracture can be defined as the threshold value u of the inclusion size $\sqrt{\text{area}}$.

Note that in the present embodiment, the average excess plot or the median excess plot is displayed on the display device 106, the operator is made to input the threshold value u, and the inclusion distribution quantifying part 201 derives the threshold value excess number of inclusions $N_u$. However, it is not necessarily to be processed as stated above. For example, the average excess plot or the median excess plot is displayed on the display device 106, and the operator may be made to input the threshold value excess number of inclusions $N_u$. Besides, the process until the threshold value excess number of inclusions $N_u$ may be performed by the operator (the inclusion distribution quantifying part 201 does not take part in the process), and the inclusion distribution quantifying part 201 may input the threshold value u and the threshold value excess number of inclusions $N_u$. Further, the threshold value excess number of inclusions $N_u$ may be found from plural samples. In such a case, the threshold value u is to be set after the inclusion sizes $\sqrt{\text{area}}$ extracted from the respective samples are all added. At this time, when a threshold value for each of the samples is defined as "$U_s$", it goes without saying that the threshold value u is a value exceeding the threshold value $u_s$.

Next, the inclusion distribution quantifying part 201 derives the coefficients $\xi$, $\sigma$ of the generalized Pareto distribution from the actual measurement data. In the present embodiment, the coefficients $\xi$, $\sigma$ of the generalized Pareto distribution are derived by using a maximum likelihood method. Hereinafter, an example of a deriving method of the coefficients ξ, σ of the generalized Pareto distribution in the present embodiment is briefly described.

A distribution function H(y) of the generalized Pareto distribution is as represented by the following formula (5). Then, a likelihood function L(σ, ξ) is represented by a product of a density function h(y) represented by the following formula (6), and it is represented by the following formula (7) when the number of samples is set to be "n". Here, the threshold value excess number of inclusions $N_u$ is given to the number of samples n, and (x−u) is given to a variable y (where "x" is the inclusion size $\sqrt{area}$, "u" is the threshold value).

[Numerical Formula 2]

$$H(y) = \begin{cases} 1 - \left(1 + \xi \frac{y}{\sigma}\right)^{-\frac{1}{\xi}} \\ \text{where } \left(1 + \xi \frac{y}{\sigma}\right) > 0, \quad \xi \neq 0 \text{(Beta Distribution, Pareto Distribution)} \\ 1 - \exp\left(-\frac{y}{\sigma}\right) \text{ where } \quad \xi = 0 \text{(Exponential Distribution)} \end{cases} \quad (5)$$

$$h(y) = \begin{cases} 1 \Big/ \sigma\left(1 + \xi \frac{y}{\sigma}\right)^{-\frac{1}{\xi}-1} \text{ where } \left(1 + \xi \frac{y}{\sigma}\right) > 0, \quad \xi \neq 0 \\ 1/\sigma \exp\left(-\frac{y}{\sigma}\right) \text{ where } \quad \xi = 0 \end{cases} \quad (6)$$

$$L(\sigma, \xi) = \begin{cases} \prod_{i=1}^{n} \left\{\frac{1}{\sigma}\left(1 + \xi \frac{y_i}{\sigma}\right)^{-\frac{1}{\xi}-1}\right\} \text{ where } \left(1 + \xi \frac{y_i}{\sigma}\right) > 0, \quad \xi \neq 0 \\ \prod_{i=1}^{n} \left\{\frac{1}{\sigma}\left(\exp\left(-\frac{y_i}{\sigma}\right)\right)\right\} \text{ where } \quad \xi = 0 \end{cases} \quad (7)$$

To simplify the calculation, the likelihood function L(σ,ξ) is treated as a log likelihood l(σ, ξ) represented by the following formula (8), and the coefficients ξ, σ in which the log likelihood l(σ, ξ) becomes the maximum are derived. In the present embodiment, the inclusion distribution quantifying part 201 derives the coefficients ξ, σ of the distribution function and the density function of the inclusion size $\sqrt{area}$ as stated above.

[Numerical Formula 3]

$$l(\sigma, \xi) = \ln(L(\sigma, \xi)) = \begin{cases} -n \cdot \ln \sigma - \left(1 + \frac{1}{\xi}\right)\sum_{i=1}^{n}\left(1 + \xi \frac{y_i}{\sigma}\right) \text{ where } \left(1 + \xi \frac{y_i}{\sigma}\right) > 0, \quad \xi \neq 0 \\ -n \cdot \ln \sigma - \frac{1}{\sigma}\sum_{i=1}^{n} y_i \text{ where } \quad \xi = 0 \end{cases} \quad (8)$$

The inclusion distribution quantifying part 201 can be enabled by using, for example, the CPU 101, the ROM 102, the RAM 103, the PD 104, the HD 105, the display device 106, and the communication I/F 108.

<Virtual Cell Unit Volume Deriving Part 202>

In the present embodiment, the machine component to be the investigation object of the fatigue strength excess probability is equally divided by $N_{V0}$ pieces of virtual cells each containing one inclusion whose inclusion size $\sqrt{area}$ exceeds "0" (zero) and having a virtual unit volume $V_0$, and the fatigue strength excess probability is calculated by each virtual cell as described below. The virtual cell unit volume deriving part 202 is one to derive the virtual unit volume $V_0$ of the virtual cell.

Figure 3:
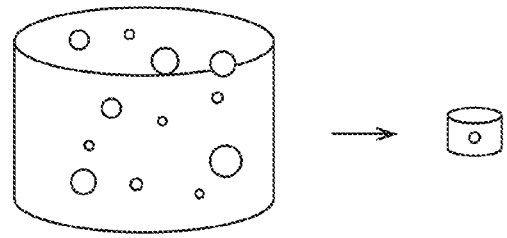
FIG. 3 is a view conceptually illustrating a virtual unit volume of a virtual cell.

FIG. 3 is a view conceptually illustrating the virtual unit volume $V_0$ of the virtual cell. As illustrated in FIG. 3, one in which the virtual unit volume $V_0$ of the virtual cell is multiplied by the number of inclusions $N_0$ contained in the sample is the volume $V_s$ of the sample. The volume $V_s$ of the sample is input by the operation of the operator.

Figure 4:
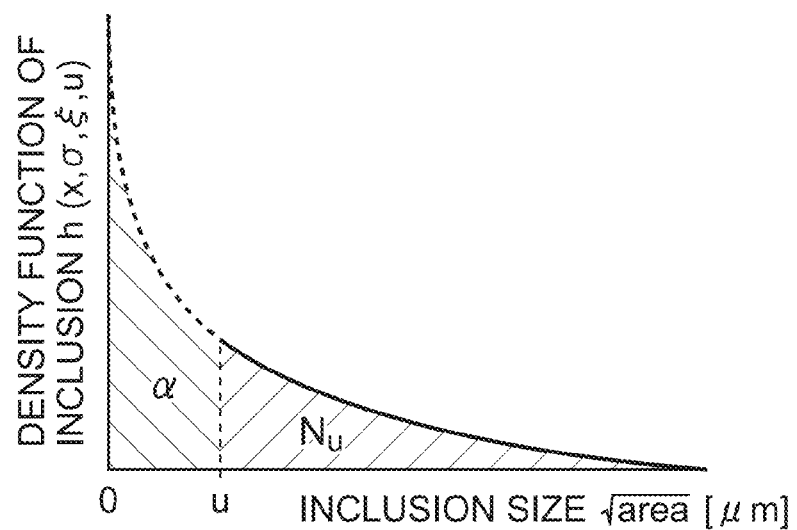
FIG. 4 is a view conceptually illustrating an example of a density function of an inclusion size.

As stated above, in the present embodiment, the distribution function of the inclusion size $\sqrt{area}$ follows the generalized Pareto distribution. FIG. 4 is a view conceptually illustrating an example of the density function h(x, σ, ξ, u) of the inclusion size $\sqrt{area}$.

A value in which the density function h(x, σ, ξ, u) of the inclusion size $\sqrt{area}$ defined by the coefficients ξ, σ a derived by the inclusion distribution quantifying part 201 is integrated within an integration range from the time when the inclusion size $\sqrt{area}$ is the threshold value u to ∞ is 1. When the density function h(x, σ, ξ, u) of the inclusion size $\sqrt{area}$ is integrated within an integration range from the time when the inclusion size $\sqrt{area}$ is "0" (zero) to ∞, a virtual inclusion ratio λ is obtained as the following formula (9).

[Numerical Formula 4]

$$\lambda = \frac{N_0}{N_u} = \begin{cases} \int_0^\infty h(x, u) dx = \left(1 - \xi\frac{u}{\sigma}\right)^{-\frac{1}{\xi}} \text{ where } \left(1 - \xi\frac{u}{\sigma}\right) > 0, \quad \xi \neq 0 \\ \int_0^\infty h(x, u) dx = \exp\left(\frac{u}{\sigma}\right) \text{ where } \quad \xi = 0 \end{cases} \quad (9)$$

As represented in the formula (9) and FIG. 4, the virtual inclusion ratio λ is one representing a proportion of the number of inclusions $N_0$ whose inclusion size $\sqrt{area}$ exceeds "0" (zero) (a zero excess number of inclusions $N_0$) within the volume $V_s$ of the sample relative to the number of inclusions $N_u$ whose inclusion size $\sqrt{area}$ exceeds the threshold value u (the threshold value excess number of inclusions $N_u$). The virtual unit volume $V_0$ of the virtual cell is represented by the following formula (10) when the virtual inclusion ratio λ is used.

$$V_0 = V_s/N_0 = V_s/(\lambda N_u) \quad (10)$$

Note that "α" is the number of inclusions whose inclusion size $\sqrt{area}$ is within a range of "0" (zero) to the threshold value u in FIG. 4.

Figure 5:
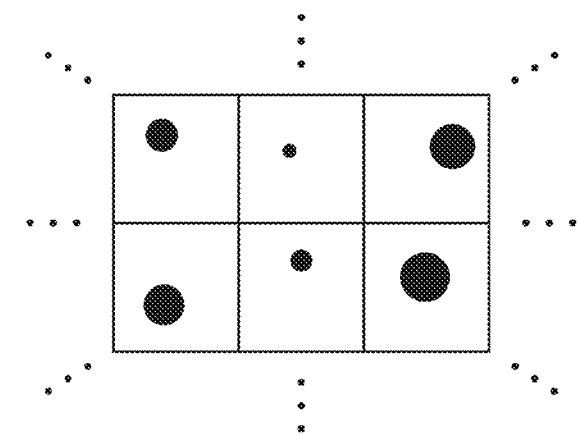
FIG. 5 is a view conceptually illustrating an example of the virtual cell.
Figure 6:
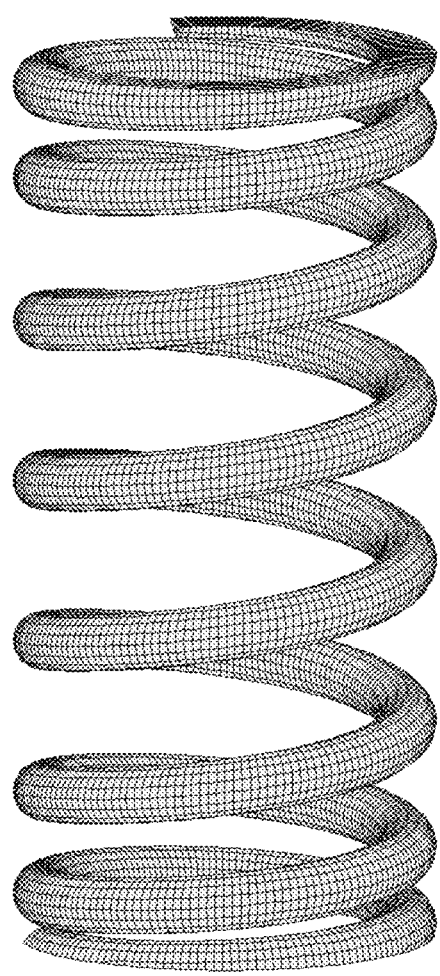
FIG. 6 is a view conceptually illustrating an outline of the machine component divided by the virtual cells.

FIG. 5 is a view conceptually illustrating an example of the virtual cell, and FIG. 6 is a view conceptually illustrating an outline of the machine component (spring) divided by the virtual cells.

One rectangle region illustrated in FIG. 5 (one mesh area illustrated in FIG. 6) is the virtual cell having the virtual unit volume $V_0$, and the region of the machine component to be the investigation object of the fatigue strength excess probability is divided by the $N_{V0}$ pieces of (same) virtual cells. One inclusion whose inclusion size $\sqrt{area}$ exceeds "0" (zero) is contained in each virtual cell, and the inclusion size $\sqrt{area}$ is distributed according to the density function of the inclusion size $\sqrt{area}$.

The virtual cell unit volume deriving part 202 derives the virtual unit volume $V_0$ of the virtual cell as stated above, and sets the $N_{V0}$ pieces of virtual cells each having the virtual unit volume $V_0$ for the machine component to be the investigation object of the fatigue strength excess probability.

Here, the number of virtual cells $N_{V0}$ is represented by the following formula (11).

$$N_{V0}=(V/V_s)\cdot N_u \cdot \lambda \tag{11}$$

In the formula (11), "V" is a volume [mm³] of the machine component to be the investigation object of the fatigue strength excess probability, and it is input by the operator.

The virtual cell unit volume deriving part 202 can be enabled by using, for example, the CPU 101, the ROM 102, the RAM 103, and the PD 104.

<Estimated Fatigue Strength Deriving Part 203>

In the present embodiment, a stress amplitude $\sigma_w$ [N/mm²] of the fatigue strength being the fatigue strength starting from the inclusion existing in the machine component and relative to a predetermined number of repetitions when a predetermined load is repeatedly applied on the machine component is represented by a function of the inclusion size $\sqrt{area}$, a Vickers hardness Hv, and a stress ratio R [-]. Note that in the following description, "the stress amplitude $\sigma_w$ of the fatigue strength being the fatigue strength starting from the inclusion existing in the machine component of a steel product and so on and relative to the predetermined number of repetitions when the predetermined load is repeatedly applied on the machine component" is abbreviated as "the stress amplitude $\sigma_w$ of the fatigue strength" according to need.

In the present embodiment, the predetermined number of repetitions of the load repeatedly applied on the machine component is assumed to be approximately for $10^7$ times, and the stress amplitude $\sigma_w$ of the fatigue strength is represented by the following formula (12).

$$\sigma_w=\{1.56\times(Hv+120)/(\sqrt{area}_{max})^{1/6}\}\times\{(1-R)/2\}^\gamma \tag{12}$$

Note that the formula (12) is originally the formula estimating the fatigue limit, but the formula (12) is used as the formula of the fatigue strength at approximately $10^7$ times in consideration of capacity of a test machine at the research time, and so on.

In the formula (12), "Hv" is the Vickers hardness. Besides, "R" is the stress ratio, and it is represented by the following formula (13). Besides, "γ" is an influence multiplier of the hardness, and it is represented by the following formula (14).

$$R=(\sigma_m-\sigma_w)/(\sigma_m+\sigma_w) \tag{13}$$

$$\gamma=0.226+Hv/10000 \tag{14}$$

In the formula (13), "$\sigma_m$" is a stress amplitude [N/mm²] of the mean stress of the machine component.

A value of the Vickers hardness Hv is obtained from a test result of the material constituting the component. Besides, values of the mean stress $\sigma_m$ and the stress ratio R of the component are obtained from the load applied on the component and the size of the component. In the present embodiment, a stress ratio of an equivalent stress at each position in the component or a stress ratio of a principal stress in a direction where a variation of the principal stress at each position in the component becomes the maximum is used as the stress ratio R. It is possible to appropriately determine in accordance with the component and so on as for either one of the above is to be used. The inclusion size $\sqrt{area}$ is defined by the distribution function (refer to the formula (1) or the formula (2)) of the inclusion size $\sqrt{area}$ defined by the coefficients ξ, a derived by the inclusion distribution quantifying part 201.

The estimated fatigue strength deriving part 203 inputs these values based on the operation and so on by the operator to perform the calculation of the formula (12), and derives the stress amplitude $\sigma_w$ of the fatigue strength at each virtual cell set for the machine component when the predetermined repetitive loads for the predetermined number of repetitions are applied on the machine component, relative to the stress ratio R at the virtual cell.

In the present embodiment, the stress amplitudes $\sigma_w$ of the fatigue strength as stated above are plurally derived while making the inclusion size $\sqrt{area}_{max}$ and the stress ratio R whose value changes in accordance with the virtual cell and a used stress condition different from one another. It is thereby possible to derive the stress amplitude $\sigma_w$ of the fatigue strength by each virtual cell for the inclusion size $\sqrt{area}_{max}$ of the inclusion existing in the machine component.

Note that in the present embodiment, the stress amplitude $\sigma_w$ of the fatigue strength is derived by the formula (12). However, the stress amplitude $\sigma_w$ of the fatigue strength is not necessarily the one as represented by the formula (12) as long as it can be represented by a function of the inclusion size $\sqrt{area}$, the Vickers hardness Hv, and the stress ratio R. For example, the stress amplitude $\sigma_w$ of the fatigue strength may be represented by the following formula (15) as described in "'Effect of inclusion on rotating bending fatigue strength of carburized and shot-peened steels for gear use' written by MATSUMOTO and so on, Proceedings of the Japan Society of Mechanical Engineers Conference on Material Mechanics, No. 900-86, 1990, p. 275 to p. 277"

$$\sigma_w=\{1.56\times(Hv+120)/(\sqrt{area}_{max})^{1/6}\}-0.5\times\sigma_m \tag{15}$$

Note that in the formula (15), the stress amplitude $\sigma_w$ of the fatigue strength is represented by using not the stress ratio R but the stress amplitude $\sigma_m$ of the mean stress of the component. However, as represented in the formula (13), the stress amplitude $\sigma_m$ of the mean stress of the component can be represented by the stress amplitude $\sigma_w$ of the fatigue strength and the stress ratio R, and therefore, the formula (15) is equivalent to be the function of the stress ratio R. In addition, the coefficients represented in the formula (12) and the formula (15) can be changed.

Besides, the Vickers hardness Hv represented in the formula (12) and the formula (15) has a correlation with the strength [N/mm²] of the material of the component. Accordingly, the stress amplitude $\sigma_w$ of the fatigue strength may be represented by using the strength of the material of the component instead of the Vickers hardness Hv. Besides, the formula (12) and the formula (15) are general formulas relating to steel materials, and therefore, it is possible to enable higher accuracy by creating and using a function in accordance with fatigue characteristics of an evaluation object material by modifying these formulas and using the stress ratio, the hardness, and the inclusion size as parameters.

The estimated fatigue strength deriving part 203 can be enabled by using, for example, the CPU 101, the ROM 102, the RAM 103, the PD 104, and the HD 105.

<Operating Stress Amplitude Deriving Part 204>

The operating stress amplitude deriving part 204 derives the stress amplitude $\sigma_p$ of the operating stress acting on each virtual cell set for the machine component when the repetitive load is applied on the machine component with a loading condition P set in advance by the operator. Note that in the following description, "the stress amplitude $\sigma_p$ of the operating stress acting on each virtual cell set for the machine component when the repetitive load is applied on the machine component with the loading condition P set in advance by the operator" is abbreviated as "the stress amplitude $\sigma_p$ of the operating stress acting on each virtual cell of the machine component" or "the stress amplitude $\sigma_p$ of the operating stress" according to need. Here, the loading condition P represents what kind of repetitive load is applied on the machine component.

The operating stress amplitude deriving part 204 inputs information of the machine component such as a shape of the machine component, the loading condition P, and strength of the material constituting the machine component (for example, a tensile strength, a yield stress, and work hardening properties). The operating stress amplitude deriving part 204 acquires these machine component information based on the operation of the operator, the communication with the external devices, and so on.

The operating stress amplitude deriving part 204 derives a change of each stress component at each virtual cell of the machine component when the repetitive load is applied on the machine component with the loading condition P set in advance by the operator by using the acquired machine component information. The change of each stress component at each virtual cell of the machine component can be derived by performing, for example, an analysis by using an FEM (Finite Element Method), a BEM (Boundary Element Method), and a calculation by using the material mechanics. Besides, there is a case when an internal stress occurs at the machine component even under a no-load state (a state when no load is applied) because a heat treatment, a plastic working, a shot peening process, or the like is performed for the machine component. This internal stress can be measured by, for example, a method in which a measurement of a residual stress by X-ray and an electrolytic polishing are alternately performed, and so on. The internal stress under the no-load state is added to the change of each stress component at each virtual cell of the machine component when the repetitive load is applied with the loading condition P set in advance by the operator by using the method of the material mechanics, and thereby, it is possible to make the fatigue design in consideration of the internal stress under the no-load state.

The operating stress amplitude deriving part 204 uses, for example, the amplitude of the equivalent stress at each virtual cell of the machine component or the amplitude of the principal stress in the direction in which the variation of the principal stress becomes the maximum at each virtual cell of the machine component as the stress amplitude $\sigma_p$ of the operating stress from the change of each stress component at each virtual cell of the machine component derived as stated above. It is possible to appropriately determine which one of the above is to be used in accordance with the machine component and so on.

In the present embodiment, the stress amplitudes $\sigma_p$ of the operating stress as stated above are plurally derived while changing the virtual cells set for the machine component. It is thereby possible to derive the stress amplitude $\sigma_p$ of the operating stress by each virtual cell set for the machine component.

Note that a half of the equivalent stress based on a value in which a minimum value is subtracted from a maximum value of a load amplitude applied on the machine component may be set as the stress amplitude $\sigma_p$ of the operating stress, or a half of a value in which an equivalent stress based on the minimum value of the load amplitude is subtracted from an equivalent stress based on the maximum value of the load amplitude applied on the machine component may be set as the stress amplitude $\sigma_p$ of the operating stress.

The operating stress amplitude deriving part 204 can be enabled by using, for example, the CPU 101, the ROM 102, the RAM 103, the PD 104, and the HD 105.

<Fatigue Strength Excess Probability Deriving Part 205>

The fatigue strength excess probability deriving part 205 reads out "the stress amplitudes $\sigma_w$ of the fatigue strength by each inclusion size $\sqrt{area}$, by each virtual cell" derived by the estimated fatigue strength deriving part 203 and "the stress amplitude $\sigma_p$ of the operating stress by each virtual cell" derived by the operating stress amplitude deriving part 204. The fatigue strength excess probability deriving part 205 sets a fatigue strength determination function $f(\sigma_p, \sigma_w)$ defined by the following formula (16).

$$f(\sigma_p, \sigma_w) = (\sigma_p > \sigma_w \text{ then } 1, \sigma_p \leq \sigma_w \text{ then } 0) \quad (16)$$

The fatigue strength determination function $f(\sigma_p, \sigma_w)$ represented by the formula (16) is set by each virtual cell, and it becomes "1" when the stress amplitude $\sigma_p$ of the operating stress of the virtual cell exceeds a value of the stress amplitude $\sigma_w$ of the fatigue strength of the virtual cell, and otherwise, becomes "0" (zero). The stress amplitude $\sigma_w$ of the fatigue strength of the virtual cell is obtained by each inclusion size $\sqrt{area}$. Accordingly, a value of the fatigue strength determination function $f(\sigma_p, \sigma_w)$ is obtained by each inclusion size $\sqrt{area}$ as for one virtual cell.

Figure 7A:
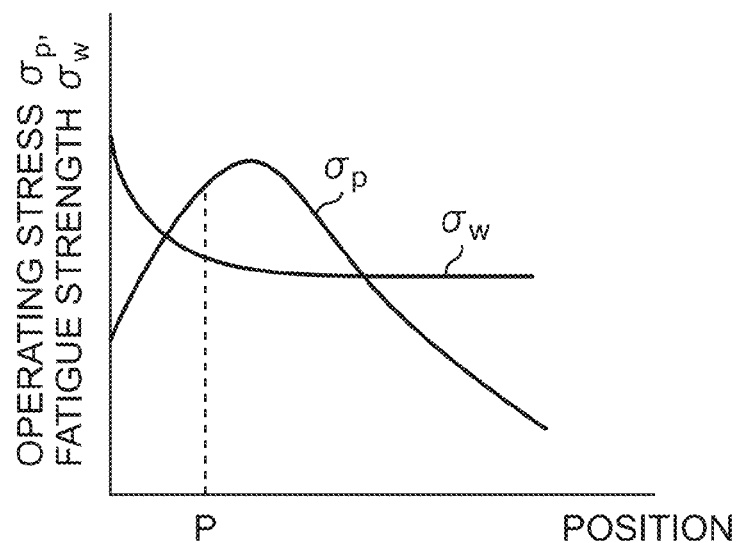
FIG. 7A is a view conceptually illustrating an example of a relationship between a stress amplitude of an operating stress and a stress amplitude of a fatigue strength, and a position of the machine component when an inclusion size is relatively large.
Figure 7B:
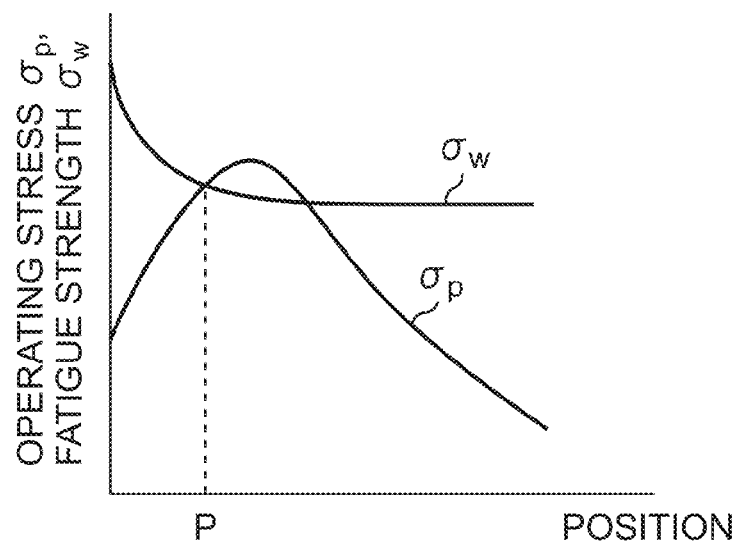
FIG. 7B is a view conceptually illustrating an example of a relationship between the stress amplitude of the operating stress and the stress amplitude of the fatigue strength, and the position of the machine component when an inclusion size $\sqrt{area}$ is relatively middle-sized.
Figure 7C:
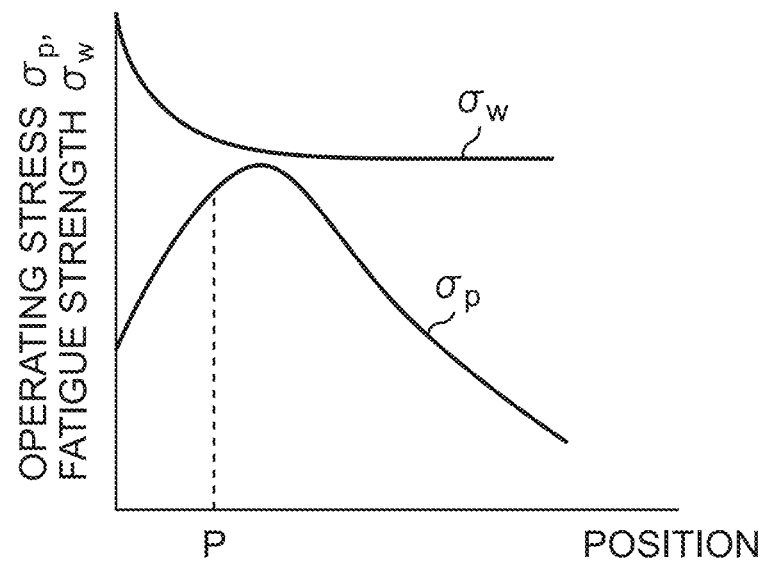
FIG. 7C is a view conceptually illustrating an example of a relationship between the stress amplitude of the operating stress and the stress amplitude of the fatigue strength, and the position of the machine component when the inclusion size $\sqrt{area}$ is relatively small.

FIGS. 7A to 7C are views conceptually illustrating an example of a relationship among the stress amplitude $\sigma_p$ of the operating stress and the stress amplitude $\sigma_w$ of the fatigue strength, and a position of the machine component. FIG. 7A illustrates the relationship when the inclusion size $\sqrt{area}$ is relatively large, FIG. 7B illustrates the relationship when the inclusion size $\sqrt{area}$ is relatively middle-sized, and FIG. 7C illustrates the relationship when the inclusion size $\sqrt{area}$ is relatively small.

As illustrated in FIG. 7A, when the inclusion size $\sqrt{area}$ existing at a virtual cell locating at a position P is large, the stress amplitude $\sigma_p$ of the operating stress at the virtual cell exceeds the value of the stress amplitude $\sigma_w$ of the fatigue strength at the virtual cell, and the value of the fatigue strength determination function $f(\sigma_p, \sigma_w)$ becomes "1". On the other hand, as illustrated in FIG. 7B, FIG. 7C, when the inclusion size $\sqrt{area}$ existing at the virtual cell locating at the position P is small, the stress amplitude $\sigma_p$ of the operating stress at the virtual cell is below the value of the stress amplitude $\sigma_w$ of the fatigue strength at the virtual cell, and the value of the fatigue strength determination function $f(\sigma_p, \sigma_w)$ becomes "0" (zero).

As stated above, the fatigue strength determination function $f(\sigma_p, \sigma_w)$ is found by each inclusion size $\sqrt{area}$ as for one virtual cell, and thereby, it is possible to obtain the inclusion size $\sqrt{area}$ at each virtual cell in which the stress amplitude $\sigma_p$ of the operating stress at the virtual cell exceeds the stress amplitude $\sigma_w$ of the fatigue strength at the virtual cell. At the virtual cell existing at the position P illustrated in each of FIGS. 7A to 7C, the stress amplitude $\sigma_p$ of the operating stress at the virtual cell exceeds the value of the stress amplitude $\sigma_w$ of the fatigue strength at the virtual cell when the inclusion size $\sqrt{area}$ larger than the inclusion size $\sqrt{area}$ when the stress amplitude $\sigma_w$ of the fatigue strength illustrated in FIG. 7B is obtained exists at the virtual cell.

Next, the fatigue strength excess probability deriving part 205 derives a fatigue strength excess probability $p_{fV}$ of the machine component as an index to determine the fatigue fracture of the machine component.

The fatigue strength excess probability is a value indicating a probability when, for example, an operating stress acting on the machine component such as the spring exceeds the fatigue strength under a certain repetitive loading condition in a giga-cycle order. In the present embodiment, it is considered that a stress state at a periphery of a certain inclusion is not affected by a stress distribution generated by neighboring inclusions, and as stated above, the machine component is made up by gathering plural virtual cells each containing one inclusion though the size thereof is not known and having the virtual unit volume $V_0$, when the fatigue strength excess probability is calculated. In the present embodiment, it is defined to have a meaning that when the fatigue fracture occurs at the machine component, the fatigue fracture occurs at any one of the virtual cells. A value obtained by subtracting a probability in which the fatigue fracture does not occur at all virtual cells from 1 is derived as the fatigue strength excess probability $p_{fV}$ of the machine component.

A fatigue strength excess probability $p_{V0}$ at a certain virtual cell having the virtual unit volume $V_0$ is represented by the following formula (17).

[Numerical Formula 5]

$$p_{V0} = \int_0^\infty \frac{h(x, \sigma, \xi, u)}{\lambda} \cdot f(\sigma_p, \sigma_w) dx \text{ where } \xi \neq 0$$
$$p_{V0} = \int_0^\infty \frac{h(x, \sigma, u)}{\lambda} \cdot f(\sigma_p, \sigma_w) dx \text{ where } \xi = 0$$
(17)

Here, $h(x, \sigma, \xi, u)/\lambda$, $h(x, \sigma, u)/\lambda$ are "an inclusion existence probability at the virtual cell" in which the density function of the inclusion size $\sqrt{area}$ is divided by a virtual inclusion ratio, and they are respectively represented by the following formula (18), formula (19).

[Numerical Formula 6]

$$\frac{h(x, \sigma, \xi, u)}{\lambda} = \left[1 \Big/ \left\{\sigma\left(1 - \xi\frac{u}{\sigma}\right)^{-\frac{1}{\xi}}\right\}\right] \cdot \left[\frac{1}{\sigma}\left\{1 + \xi\frac{(x-u)}{\sigma}\right\}^{-\frac{1}{\xi}-1}\right]$$ (18)

where
$$\int_u^\infty h(x, \sigma, \xi, u) dx = 1, \left\{1 + \xi\frac{(x-u)}{\sigma}\right\} > 0,$$
$\xi \neq 0$ $$\frac{h(x, \sigma, u)}{\lambda} = \frac{1}{\sigma \cdot \exp\left(\frac{x}{\sigma}\right)}$$ (19)

where
$$\int_u^\infty h(x, \sigma, u) dx = 1,$$
$\xi = 0$

Figure 8:
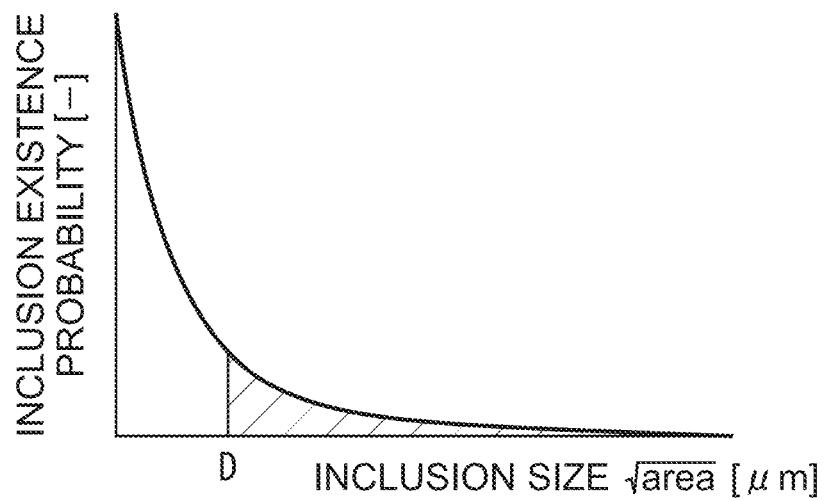
FIG. 8 is a view conceptually illustrating an example of a relationship between an inclusion existence probability and the inclusion size at the virtual cell.

FIG. 8 is a view conceptually illustrating an example of a relationship between the inclusion existence probability and the inclusion size $\sqrt{area}$ at the virtual cell.

An area of an oblique region illustrated in FIG. 8 represents the fatigue strength excess probability $p_{V0}$ at one virtual cell. "D" in FIG. 8 represents the inclusion size $\sqrt{area}$ in which the stress amplitude $\sigma_p$ of the operating stress at the virtual cell exceeds the stress amplitude $\sigma_w$ of the fatigue strength at the virtual cell, and it corresponds to the inclusion size $\sqrt{area}$ when the stress amplitude $\sigma_w$ of the fatigue strength illustrated in FIG. 7B is obtained.

The probability in which the fatigue strength is exceeded as a whole of the machine component, namely, the fatigue strength excess probability $p_{fV}$ at the whole of the machine component made up of all virtual cells is represented by the following formula (20).

[Numerical Formula 7]

$$p_{fV} = 1 - \pi_{i=1}^{N_{V0}}(1 - p_{V0})$$ (20)

In the formula (20), "i" is a variable [–] identifying the virtual cell.

As stated above, the fatigue strength excess probability $p_{fV}$ of the machine component is the value where the probability in which the fatigue fracture does not occur at all virtual cells is subtracted from "1" (refer to a right side of the formula (20)).

The fatigue strength excess probability deriving part 205 derives the fatigue strength excess probability $p_{fV}$ of the whole of the machine component as stated above.

The fatigue strength excess probability deriving part 205 can be enabled by using, for example, the CPU 101, the ROM 102, and the RAM 103.

<Fatigue Strength Excess Probability Output Part 206>

The fatigue strength excess probability output part 206 displays the value of the fatigue strength excess probability $p_{fV}$ of the whole of the machine component derived by the fatigue strength excess probability deriving part 205 on a display device, transmits to external devices, or stores at a storage media based on instructions by the operator. For example, a design of the machine component (an external force as use conditions, the shape of the machine component, determination of materials and so on constituting the machine component) is performed so that the fatigue strength excess probability $p_{fV}$ of the whole of the machine component becomes a predetermined value, and it is possible to manufacture the machine component according to the design, as a way of using the fatigue strength excess probability $p_{fV}$ of the whole of the machine component. Besides, it is possible to derive the value of the fatigue strength excess probability $p_{fV}$ for the whole of the machine component to estimate a fracture cause of the machine component why the fatigue fracture occurred in the past.

The fatigue strength excess probability output part 206 can be enabled by using, for example, the CPU 101, the ROM 102, the RAM 103, the PD 104, the HD 105, the display device 106, and the communication I/F 108.

Figure 9:
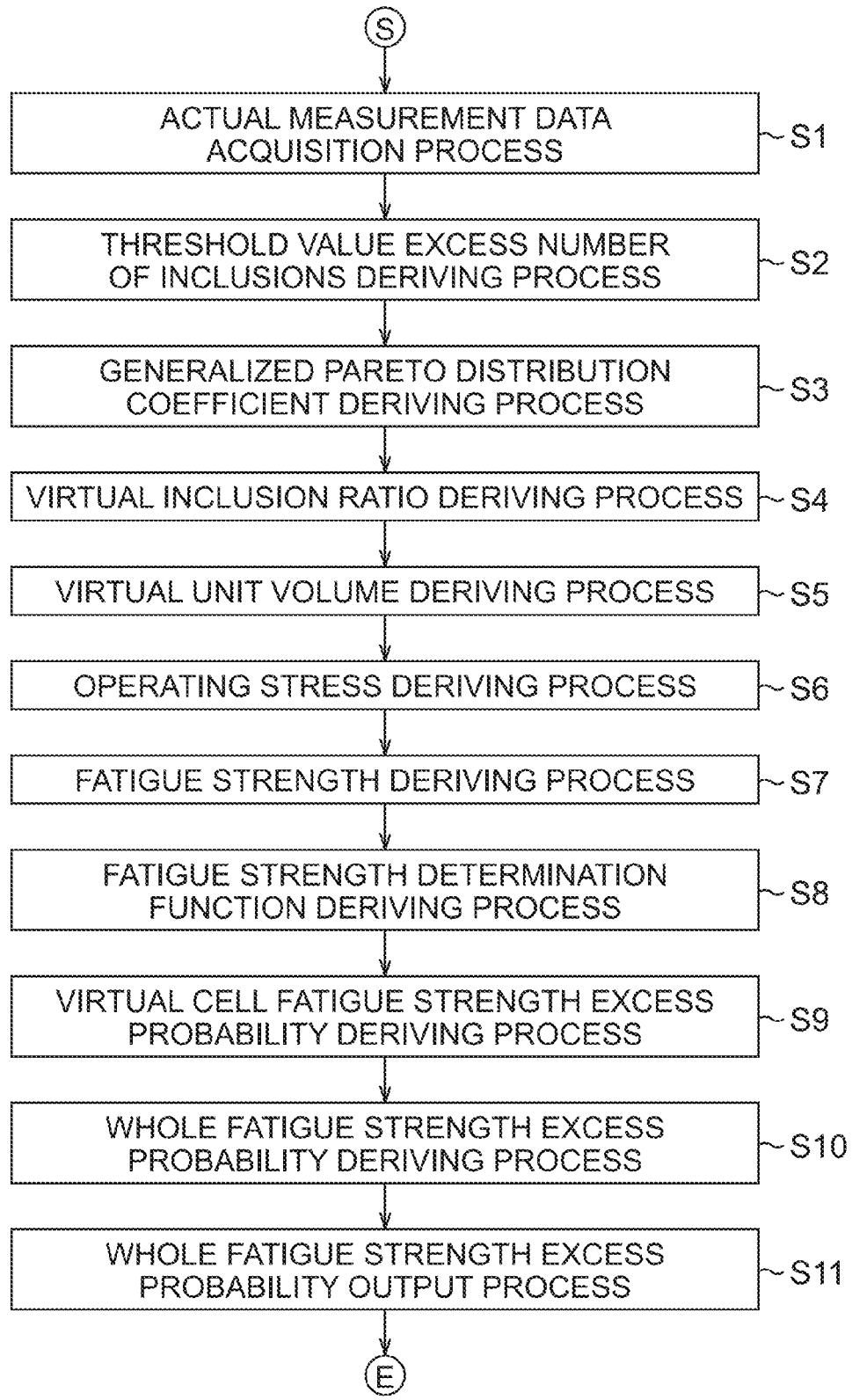
FIG. 9 is a flowchart explaining an example of a flow of operations of the component fatigue fracture evaluation device.

Next, an example of a flow of operations of the component fatigue fracture evaluation device 100 is described with reference to a flowchart in FIG. 9.

At first, in step S1, the inclusion distribution quantifying part 201 performs an actual measurement data acquisition process. Specifically, the inclusion distribution quantifying part 201 acquires information of the inclusion size $\sqrt{area}$ of a sample (made up of the same kind of material as the machine component) obtained by the slime method and so on as the actual measurement data.

Next, in step S2, the inclusion distribution quantifying part 201 performs a threshold value excess number of inclusions deriving process. Specifically, the inclusion distribution quantifying part 201 creates and displays the average excess plot or the median excess plot by using the actual measurement data obtained in the step S1. The inclusion distribution quantifying part 201 inputs the threshold value u visually defined by the operator based on the average excess plot or the median excess plot, and derives the number of inclusions exceeding the threshold value u as the threshold value excess number of inclusions $N_u$ from the actual measurement data.

Next, in step S3, the inclusion distribution quantifying part 201 performs a generalized Pareto distribution coefficient deriving process. Specifically, the inclusion distribution quantifying part 201 derives the coefficients $\xi$, $\sigma$ a in which the log likelihood $l(\sigma, \xi)$ in the formula (8) becomes the maximum based on the actual measurement data obtained in the step S1 and the threshold value u derived in the step S2.

Next, in step S4, the virtual cell unit volume deriving part 202 performs a virtual inclusion ratio deriving process. Specifically, the virtual cell unit volume deriving part 202 performs the calculation of the formula (9) to derive the virtual inclusion ratio $\lambda$ based on the threshold value u derived in the step S2 and the coefficients $\xi$, $\sigma$ derived in the step S3.

Next, in step S5, the virtual cell unit volume deriving part 202 performs a virtual unit volume deriving process. Specifically, the virtual cell unit volume deriving part 202 inputs the volume $V_s$ of the sample, performs the calculation of the formula (10) to derive the virtual unit volume $V_0$ of the virtual cell based on the volume $V_s$ of the sample, the threshold value excess number of inclusions $N_u$ derived in the step S2, and the virtual inclusion ratio $\lambda$ derived in the step S4. Besides, the virtual cell unit volume deriving part 202 inputs the volume V of the machine component, performs the calculation of the formula (11) to derive the number of virtual cells $N_{V0}$ based on the volume V of the machine component, the volume $V_s$ of the sample, the threshold value excess number of inclusions $N_u$ derived in the step S2, and the virtual inclusion ratio $\lambda$ derived in the step S4. The virtual cell unit volume deriving part 202 sets the virtual cells for the machine component (namely, the region of the machine component is divided by the $N_{V0}$ pieces of virtual cells each having the virtual unit volume $V_0$).

Next, in step S6, the operating stress amplitude deriving part 204 performs an operating stress deriving process. Specifically, the operating stress amplitude deriving part 204 acquires the information of the machine component, and derives the change of each stress component at each virtual cell when the repetitive load is applied on the machine component with the loading condition P set in advance by the operator by using the acquired information of the machine component. The operating stress amplitude deriving part 204 derives the stress amplitude $\sigma_p$ of the operating stress acting on the machine component by each virtual cell when the repetitive load is applied on the machine component with the loading condition P set in advance by the operator from the derived change of each stress component at each virtual cell.

Next, in step S7, the estimated fatigue strength deriving part 203 performs a fatigue strength deriving process. Specifically, the estimated fatigue strength deriving part 203 inputs values of the Vickers hardness Hv, the mean stress $\sigma_m$ of the machine component, and the stress ratio R. The estimated fatigue strength deriving part 203 performs the calculation of the formula (12) based on these Vickers hardness Hv, mean stress $\sigma_m$ of the machine component, and stress ratio R, and the inclusion size $\sqrt{area}$ obtained based on the distribution function of the inclusion size $\sqrt{area}$ defined by the coefficients $\xi$, $\sigma$ a derived in the step S3. The predetermined load is repeatedly applied on the machine component, and the stress amplitude $\sigma_w$ of the fatigue strength corresponding to almost the fatigue limit when the number of repetitions becomes approximately $10^7$ times or more is derived by the calculation of the formula (12) by each virtual cell for the inclusion size $\sqrt{area}$.

Next, in step S8, the fatigue strength excess probability deriving part 205 performs a fatigue strength determination function deriving process. Specifically, the fatigue strength excess probability deriving part 205 derives the fatigue strength determination function $f(\sigma_p, \sigma_w)$ by performing the calculation of the formula (16) based on "the stress amplitude $\sigma_w$ of the fatigue strength by each inclusion size $\sqrt{area}$ and by each virtual cell" derived in the step S7 and "the stress amplitude $\sigma_p$ of the operating stress by each virtual cell" derived in the step S6.

Next, in step S9, the fatigue strength excess probability deriving part 205 performs a virtual cell fatigue strength excess probability deriving process. Specifically, the fatigue strength excess probability deriving part 205 performs the integration within the inclusion size range from "0" (zero) to infinite by using the formula (17) based on the threshold value u derived in the step S2, the coefficients $\xi$, $\sigma$ derived in the step S3, and the fatigue strength determination function $f(\sigma_p, \sigma_w)$ derived in the step S8 to derive the fatigue strength excess probability $p_{V0}$ at each virtual cell.

Next, in step S10, the fatigue strength excess probability deriving part 205 performs a whole fatigue strength excess probability deriving process. Specifically, the fatigue strength excess probability deriving part 205 performs the calculation of the formula (20) based on the fatigue strength excess probability $p_{V0}$ at individual virtual cell derived in the step S9 to derive the fatigue strength excess probability $p_{fV}$ of the whole of the machine component made up of all of the virtual cells.

Next, in step S11, the fatigue strength excess probability output part 206 performs a whole fatigue strength excess probability output process. Specifically, the fatigue strength excess probability output part 206 displays the fatigue strength excess probability $p_{fV}$ of the whole of the machine component derived in the step S10 on the display device, transmits to the external devices, and stores at the storage media based on an instruction by the operator.

As stated above, in the present embodiment, the probability in which the stress amplitude $\sigma_p$ of the operating stress exceeds the stress amplitude $\sigma_w$ of the fatigue strength (the fatigue strength excess probability $p_{V0}$ of the virtual cell) is derived at each virtual cell in which the region of the machine component is equally divided so that one inclusion is contained and the virtual unit volume $V_0$ is held on the assumption that the distribution function of the inclusion size $\sqrt{area}$ follows the generalized Pareto distribution. Then the probability in which the stress amplitude $\sigma_p$ of the operating stress exceeds the stress amplitude $\sigma_w$ of the fatigue strength (the fatigue strength excess probability $p_{fV}$ of the machine component) is derived in at least one virtual cell from the fatigue strength excess probability $p_{V0}$. It is therefore possible to figure out the fatigue strength excess probability of the machine component broken by the internal fatigue fracture starting from the inclusion. Accordingly, it is possible to enable to perform the fatigue design of the machine component in consideration of both the distribution of the inclusions existing in the machine component and the stress distribution in the machine component without performing a number of fatigue tests.

It is conceivable that this method can be applied to wide use, for example, such as an inclusion control to satisfy aimed fatigue performance and fracture probability of the machine component, a hardness control, a residual stress control, a shape, a study on a design stress by use conditions and so on. Further, in this method, it is possible to make a degree of effect of individual parameters on the other parameters clear, and it is possible to uniformly express the effects of the parameters which have been conventionally studied separately. Accordingly, this method can be an effective tool for the fatigue design of the machine component. Besides, it is possible to apply this method to evaluation of a material whose hardness is different by each portion, evaluation in consideration of a difference of effect of a kind of inclusion on the fatigue strength. Further, this method can be applied to various machine components such as a coil spring.

Here, it is necessary that the stress distribution of one virtual cell is approximately uniform. However, there is a possibility in which the virtual unit volume $V_0$ becomes large relative to the stress distribution when the number of inclusions is small or a steep stress gradient exists in the machine component. In such a case, it is possible to perform a sub virtual cell setting process in which the virtual unit volume $V_0$ is equally divided in plural to set sub virtual cells in at least one of the virtual cells. In this case, a fatigue strength excess probability $p_{Dj}$ at the sub virtual cell can be represented by the following formula (21).

[Numerical Formula 8]

$$p_{Dj} = \frac{V_{Dj}}{V_0} \cdot \int_0^\infty \frac{h(x, \sigma, \xi, u)}{\lambda} \cdot f(\sigma_{pi,j}, \sigma_w) dx \quad (21)$$

In the formula (21), "$V_{Dj}$" is a volume of the sub virtual cell, "$\sigma_{pi,j}$" is a stress amplitude of an operating stress acting on each sub virtual cell. When the number of sub virtual cells is set as "$N_D$", the fatigue strength excess probability $p_{V0}$ at the virtual cell is derived by the following formula (22), and the fatigue strength excess probability $p_{fV}$ of the machine component is derived by the following formula (23). As represented in the formula (22), the fatigue strength excess probability $p_{V0}$ at the virtual cell is one in which the fatigue strength excess probabilities $p_{Dj}$ at respective sub virtual cells represented in the formula (21) are added up. Besides, as represented by formula (23), the fatigue strength excess probability $p_{fV}$ of the machine component is one in which a probability in which all virtual cells are not fatigue fractured is subtracted from 1.

[Numerical Formula 9]

$$p_{V0} = \sum_{j=1}^{N_D} \frac{V_{Dj}}{V_0} \cdot \int_0^\infty \frac{h(x, \sigma, \xi, u)}{\lambda} \cdot f(\sigma_{pi,j}, \sigma_w) dx \quad (22)$$

$$p_{fv} = 1 - \prod_{i=1}^{N_{V0}} (1 - p_{V0}) =$$

$$1 - \prod_{i=1}^{N_{V0}} \left( 1 - \sum_{j=1}^{N_D} \frac{V_{Dj}}{V_0} \cdot \int_0^\infty \frac{h(x, \sigma, \xi, u)}{\lambda} \cdot f(\sigma_{pi,j}, \sigma_w) dx \right) \quad (23)$$

Note that in each of the formula (21) to the formula (23), a case when the distribution function of the inclusion size $\sqrt{area}$ is the Pareto distribution or the beta distribution, is represented. However, it is possible to apply for a case when the distribution function of the inclusion size $\sqrt{area}$ is the exponential distribution if the density function $h(x, \sigma, \xi, u)$ of the inclusion size $\sqrt{area}$ in each of the formula (21) to the formula (23) is set to be the density function $h(x, \sigma, u)$.

It is thereby possible to appropriately derive the fatigue strength excess probability $p_{fV}$ of the whole of the machine component even when the number of inclusions is small or the steep stress gradient exists in the machine component.

Next, examples of the present invention are described.

Example 1

At first an example 1 is described.

In the present example, a coil spring in which a compressive residual stress is introduced into a surface thereof is used as the machine component. As a material constituting the coil spring, two kinds of high-tensile spring steels (materials A, B) each of whose strength is 1900 [MPa] class (Vickers hardness: Hv=700) are used. These materials are known as materials in which the fatigue fracture starting from the inclusion existing inside thereof may occur. The material A is a material extracted from a portion where a density of the inclusion is (relatively) high, and the material B is a material extracted from a portion where the density of the inclusion is (relatively) low. These two materials A, B are wire drawn to manufacture 10 pieces each of the coil springs each of whose wire diameter is 3.3 [mm], outside diameter is 22 [mm], the number of turns is seven. Then the similar shot peening process is performed, and the residual stress is introduced into the surface of the coil spring for each of these coil springs.

Figure 10:
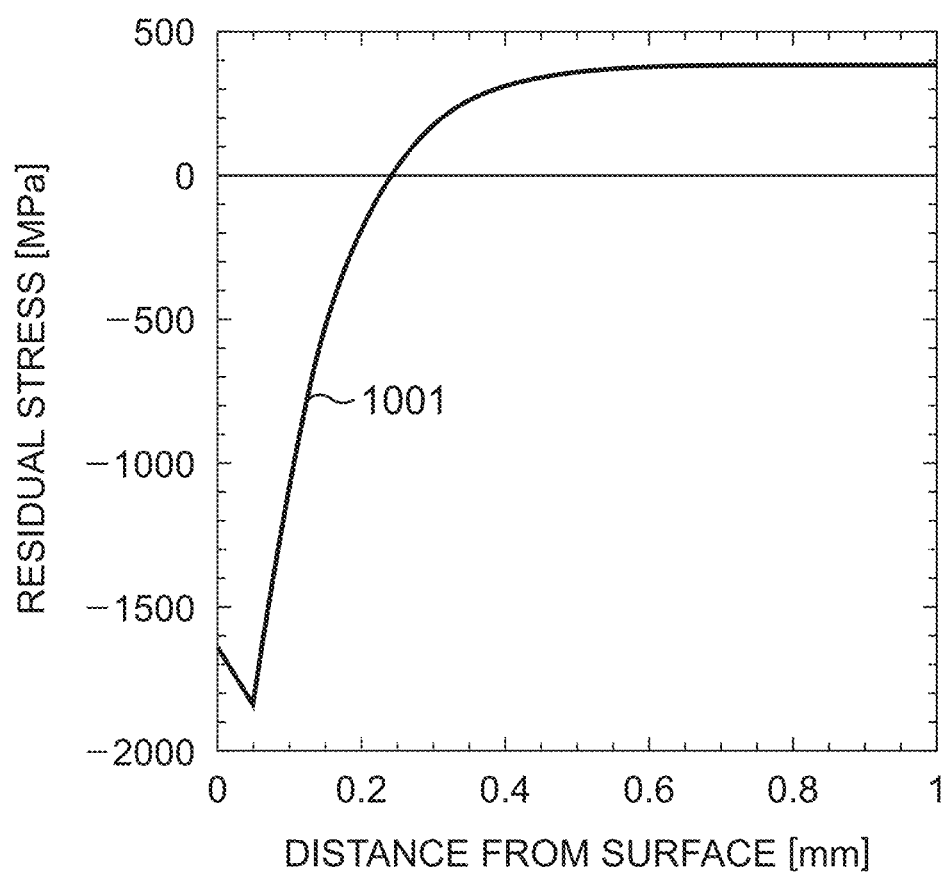
FIG. 10 is a view illustrating a relationship between a distance (depth) from a wire surface of a coil spring and a stress amplitude of a residual stress of the coil spring.

FIG. 10 is a view illustrating a relationship between a distance (depth) of the coil spring from a wire surface and a stress amplitude of the residual stress of the coil spring. In the present example, the residual stress illustrated in FIG. 10 is introduced into the coil spring.

As for the material A whose volume is 2500 [mm³], an iron part is melted and only the inclusions are extracted by using the slime extraction method. As a result, 100 pieces of inclusions each of whose inclusion size $\sqrt{area}$ is 20 [μm] or more are extracted for the material A. As for the material B whose volume is 7500 [mm³], the iron part is melted and only the inclusions are extracted by using the slime extraction method. As a result, 100 pieces of inclusions each of whose inclusion size $\sqrt{area}$ is 20 [μm] or more are extracted.

The distribution function of the inclusion size is investigated, then it turns out that it is possible to fit an actual measurement data with approximately equivalent distribution function though the volumes required for the extraction are different.

An approximate function used at this time is the exponential distribution belonging to the generalized Pareto distribution as an extreme value statistical function, and the approximate function is obtained by the maximum likelihood method. The coefficient σ thereby obtained is 5.67 (σ=5.67). Besides, 20 (u=20) is used as the threshold value u.

On the other hand, the volume V of the coil spring used for the evaluation is V=4006 [mm³] because the number of turns is 7. This coil spring is attached to a spring fatigue test device at a load of 300 [N], and a fatigue test is performed while setting a test load range at 350 [N].

As a result, seven pieces are fatigue fractured by the repetitive load tests for 500 million times in the material A, but only three pieces are fatigue fractured in the material B.

The fatigue strength excess probability $p_{fV}$ of a whole of the coil spring is estimated by using the experimental result.

From the distribution function of the inclusion sizes $\sqrt{area}$ of the materials A, B, 0.733 [mm³] is obtained as a virtual unit volume $V_{0A}$ of the material A, and 2.1 [mm³] is obtained as a virtual unit volume $V_{0B}$ of the material B, respectively.

Next, as for the coil spring of the material A, the coil spring is divided by 3409 pieces of virtual cells being the same number of inclusions assumed to exist in the evaluation object coil spring. As for the coil spring of the material B, it is possible to divide the coil spring by a third part of the number of virtual cells of the material A because the density of the inclusion is the third part of that of the material A. However, a size of the virtual cell is too large to express the residual stress distribution in a spring cross section by the shot peening in detail, and a large stress distribution is generated in one virtual cell. Accordingly, the coil spring is divided by sub virtual cells in which one virtual cell is divided into three pieces as for the coil spring of the material B.

Figure 11:
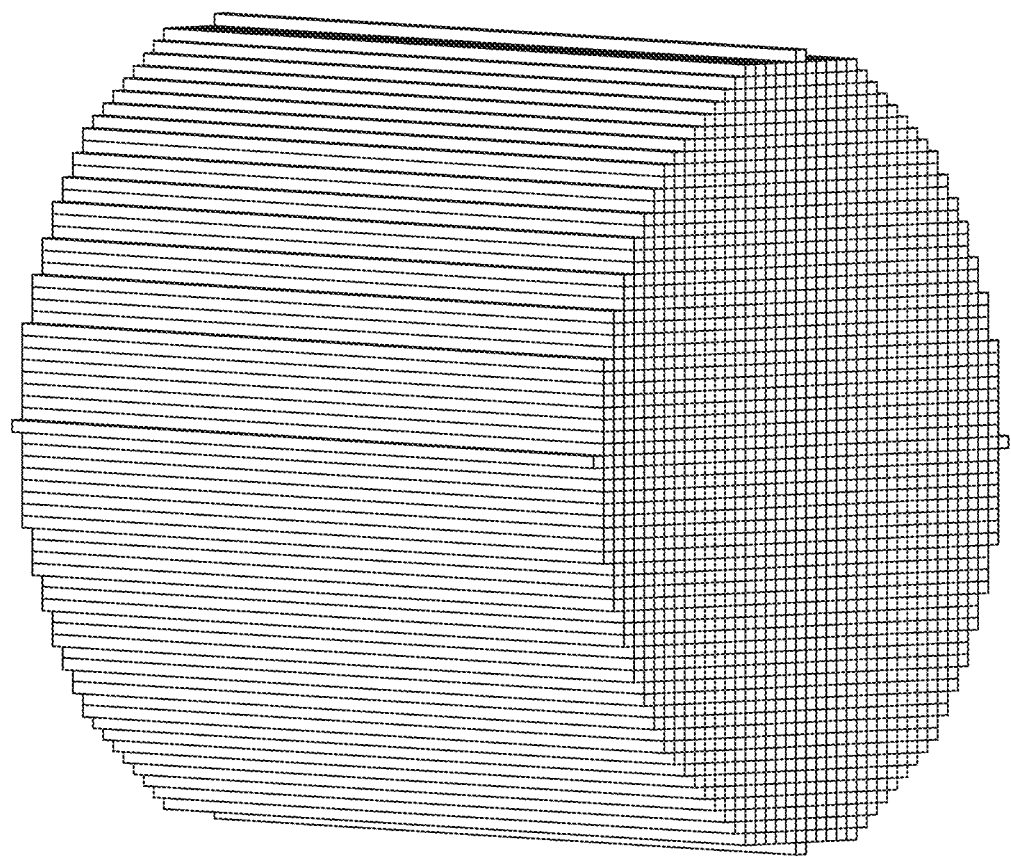
FIG. 11 is a view conceptually illustrating (a part of) the virtual cell set for the coil spring.

FIG. 11 is a view conceptually illustrating (a part of) the virtual cells set for the coil spring.

The coil spring wound at an equal pitch becomes a uniform stress state in a length direction of the wire. Accordingly, the length direction of the wire is not divided by the virtual cell. On the other hand, a cross section of the wire is minutely divided by each virtual cell so that the stress at the position can be reproduced. As for the coil spring of the material A, the 3409 pieces of virtual cells are used, and therefore, the coil spring of the material A is divided by the 3409 pieces of virtual cells in a thin strip state. As for the coil spring of the material B, the virtual cell is further divided by the three sub virtual cells, and therefore, it is divided by the 10227 (=3409× 3) pieces of sub virtual cells in the thin strip state. Each of the stress distributions of these virtual cells and the sub virtual cells becomes uniform. Besides, an inclusion existence probability at the sub virtual cell is a third part of the inclusion existence probability at the virtual cell.

Next, a formula of MURAKAMI widely used as an estimation method of the fatigue strength of the internal fatigue fracture starting from inclusion is used as a fatigue strength estimation formula (refer to the formula (12)). Note that the formula of MURAKAMI is a formula to estimate the fatigue limit, but it is known that it corresponds to the fatigue strength of approximately $10^8$ times to $10^{10}$ times from the experimental result of the present inventors. Besides, it is also verified that a change of the fatigue strength at $10^8$ times to $10^{10}$ times is extremely small to be a several % or less.

Besides, a stress ratio and an amplitude of a maximum principal stress are used as the stress used for the fatigue evaluation.

A state of the stress distribution in the coil spring can be calculated by adding up a residual stress by the shot peening as a static stress and a torsional stress corresponding to a load required to fix a length of the coil spring to a stress estimated by Wahl's theory of the coil spring as a varying stress generated in the coil spring by the repetitive load.

Figure 12:
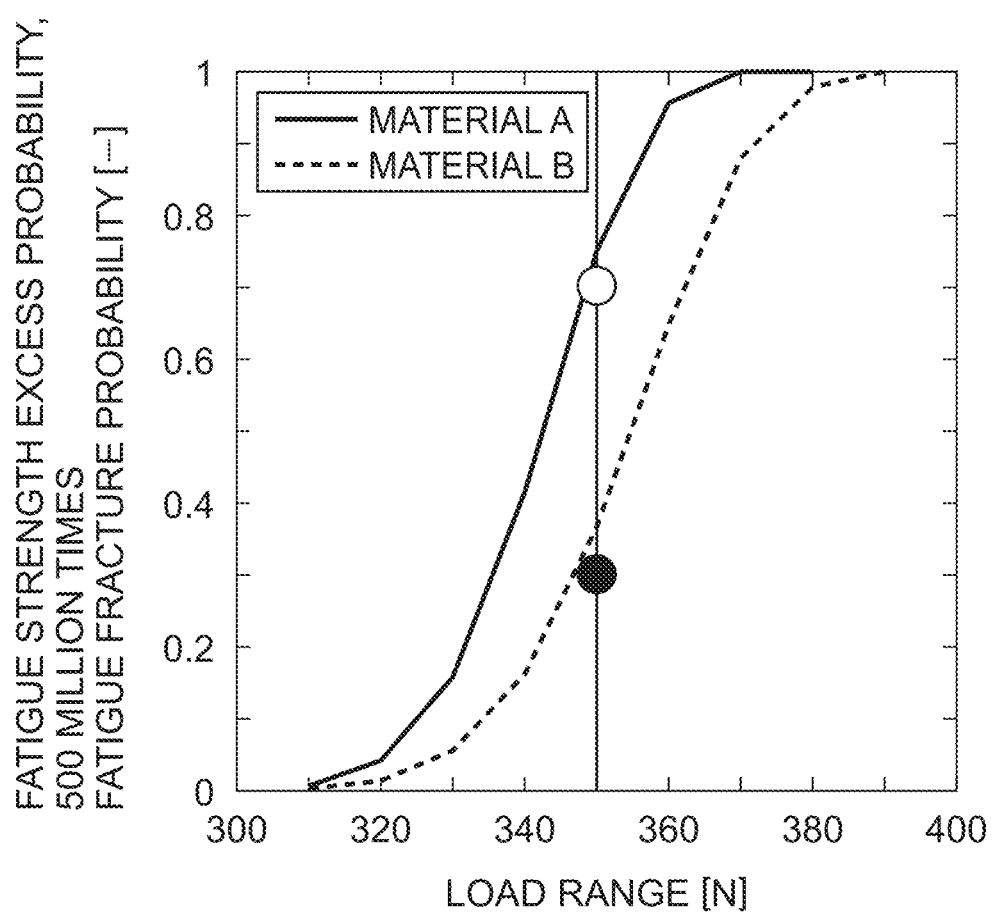
FIG. 12 is a view illustrating fatigue strength excess probabilities of coil springs of materials A, B and experimental results (500 million times fatigue fracture probability) of respective coil springs.

FIG. 12 is a view illustrating the fatigue strength excess probabilities $p_{fV}$ of the whole of the coil springs of the materials A, B estimated by the above-stated conditions and the experimental results of respective coil springs (500 million times fatigue fracture probabilities).

In FIG. 12, a solid line is the fatigue strength excess probability $p_{fV}$ of the whole of the coil spring of the material A, and a white circle is the experimental result (500 million times fatigue fracture probability) of the coil spring of the material A. Besides, a dotted line is the fatigue strength excess probability $p_{fV}$ of the whole of the coil spring of the material B, and a black circle is the experimental result (500 million times fatigue fracture probability) of the coil spring of the material B. As illustrated in FIG. 12, it can be seen that the fatigue strength excess probability $p_{fV}$ of the whole of the coil spring and the experimental result are well matched.

Example 2

Next, an example 2 is described. In the present example, a case when a rotating bending test is performed in which a tensile and compressive forces are repeatedly applied on a surface while applying a bending moment is described.

In the present example, a round bar test piece in which compressive residual stress is introduced into a surface thereof by the shot peening is used as the machine component. As a material constituting the round bar test piece, a high-tensile steel whose strength is 2200 [MPa] class (Vickers hardness: Hv=750) is used. This material is known as a material in which a fatigue fracture starting from inclusions existing inside thereof occurs.

Round bar test pieces used for a NAKAMURA rotating bending test each of whose length at a parallel part is 200 [mm], a diameter at the parallel part is 3.3 [mm] are manufactured with this material. The shot peening processes of different conditions are performed for these round bar test pieces, the residual stress introduced into each surface of the round bar test piece is changed, and effects on the fatigue characteristics are verified.

Figure 13:
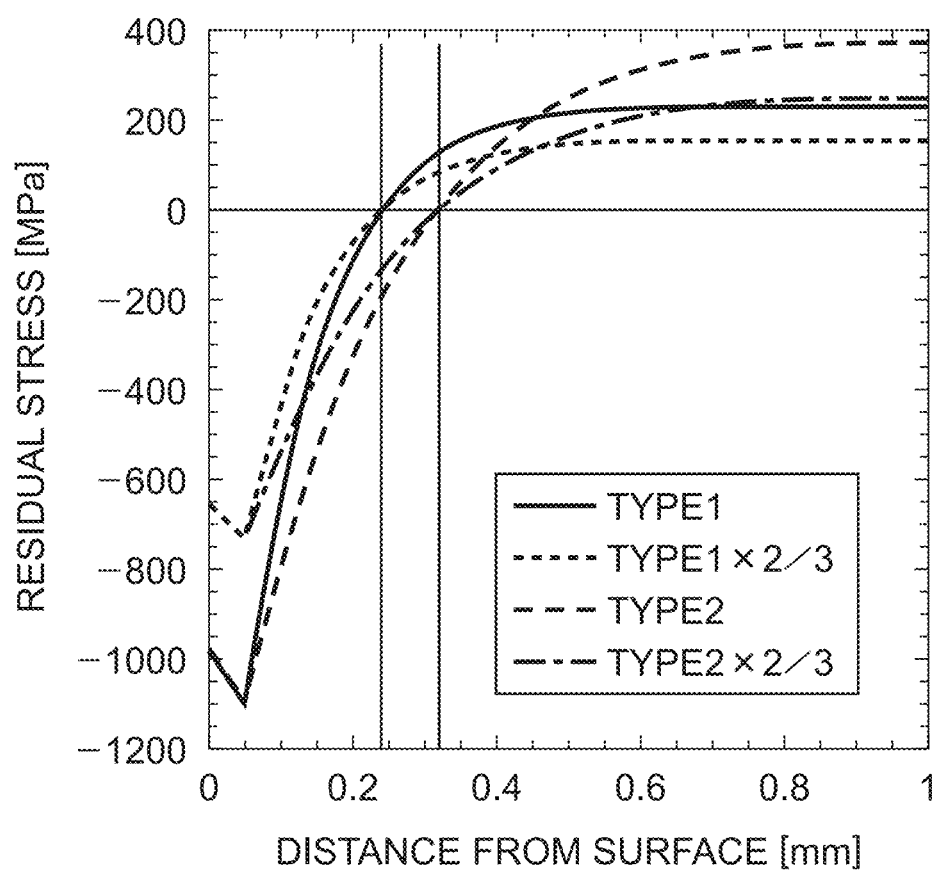
FIG. 13 is a view illustrating a relationship between a distance (depth) from a surface of a round bar test piece and a stress amplitude of a residual stress of the round bar test piece.

FIG. 13 is a view illustrating a relationship between a distance (depth) of the round bar test piece from a surface, and a stress amplitude of the residual stress of the round bar test piece. Here, the residual stress in a vicinity of a surface layer of the round bar test piece is measured, and a residual stress pattern inside the round bar test piece is found from the measured residual stress in the vicinity of the surface layer. There are five patterns in the residual stress patterns in which a size and a depth distribution of the residual stress are changed, and one of them is one in which the residual stress does not exist.

Next, as for the material (the same kind of material as the material constituting the round bar test piece) whose volume is 3000 [mm$^3$], the iron part is melted and only the inclusions are extracted by using the slime extraction method. As a result, 100 pieces of inclusions whose inclusion size $\sqrt{area}$ is 20 [μm] or more are extracted.

The beta distribution in the generalized Pareto distribution is used as the extreme value statistical function, as the distribution function of the inclusion size $\sqrt{area}$, and the approximate function is obtained by the maximum likelihood method. The coefficient ξ thereby obtained is −0.1 (ξ=−0.1), and the coefficient σ is 6.1 (σ=6.1). Besides, 20 (u=20) is used as the threshold value u.

Next, a test stress (a stress amplitude at a surface of the test piece) in which the fatigue strength excess probability $p_{fV}$ of the NAKAMURA rotating bending test piece (diameter: 3.3 [mm], bending center span: 200 [mm]) of this material becomes 50 [%] (=0.5) is estimated by a process based on a flowchart of the above-stated embodiment. The stress amplitude at the surface of the round bar test piece and the fracture probability (experimental result) of the round bar test piece whose the fatigue strength excess probability $p_{fV}$ is 50 [%] (=0.5) are represented in Table 1.

TABLE 1

| SHOTT PEENING CONDITION | WITHOUT RESIDUAL STRESS | TYPE 1 | TYPE 1 × 2/3 | TYPE 2 | TYPE 2 × 2/3 |
|---|---|---|---|---|---|
| STRESS AMPLITUDE [N/mm$^2$] | 768 | 872 | 873 | 922 | 918 |
| FRACTURE PROBABILITY [—] | 0.5 | 0.4 | 0.5 | 0.4 | 0.5 |

Next, 10 pieces each of NAKAMURA rotating bending test pieces (diameter: 3.3 [mm], bending center span: 200 mm) are manufactured with this material, and the rotating bending tests for 300 million times are performed at the stress of the calculation result. As a result, a ratio of the number of fractured test pieces (fracture probability) approximates to 0.5 (50%), and it becomes obvious that the estimated result and the experimental result are corresponding.

Note that in Table 1, it turns out that the fatigue strength is low when the shot peening is not performed, but there is a large improvement effect in the fatigue strength by performing some shot peening. Besides, in Table 1, it is indicated that there are cases when the fatigue strength changes largely by a difference in the depth of the distribution of the maximum compressive residual stress (difference between a type 1 and a type 2) than a difference of sizes of the maximum compressive residual stress introduced by the shot peening (the stress amplitude in which the fatigue strength excess probability becomes 50% does not change even if the maximum of the residual stress is set to be two thirds).

Note that the above-described embodiment of the present invention can be implemented by a computer executing a program. Further, computer program products such as a computer-readable recording medium recording such a program, and the program are also applicable as the embodiment of the present invention. As the recording medium, for example, a flexible disk, a hard disk, an optical disk, an optical magnetic disk, a CD-ROM, a magnetic tape, a non-volatile memory card, a ROM, and so on can be used.

Further, it should be noted that the above embodiments merely illustrate concrete examples of implementing the present invention, and the technical scope of the present invention is not to be construed in a restrictive manner by these embodiments. That is, the present invention may be implemented in various forms without departing from the technical spirit or main features thereof.

INDUSTRIAL APPLICABILITY

The present invention can be used for, for example, design and manufacturing of machine components, and estimation of fracture causes of the machine components.

The invention claimed is:

1. A component fracture evaluation method evaluating fracture performance of a machine component, comprising:
   analyzing a sample made up of the same kind of material as a material constituting the machine component to extract inclusions in the sample;
   a threshold value excess number of inclusions deriving process deriving a threshold value excess number of inclusions being the number of inclusions whose inclusion size exceeds a threshold value among the inclusions contained in the sample based on the inclusion size being a size of the inclusion extracted by the analysis;
   a coefficient deriving process deriving coefficients of a generalized Pareto distribution based on the inclusion size of the inclusion extracted by the analysis, the threshold value excess number of inclusions by the threshold value excess number of inclusions deriving process, and the threshold value on an assumption that a distribution function of the inclusion size of the inclusion extracted by the analysis follows the generalized Pareto distribution;
   a virtual inclusion ratio deriving process deriving a virtual inclusion ratio being a ratio between the threshold value excess number of inclusions being the number of inclusions whose inclusion size exceeds the threshold value among the inclusions contained in the sample and a zero excess number of inclusions being the number of inclusions whose inclusion size exceeds "0" (zero) among the inclusions contained in the sample; and
   a virtual unit volume deriving process deriving a virtual unit volume being a volume of a virtual cell when the machine component is equally divided by plural virtual cells each containing one inclusion based on the threshold value excess number of inclusions, the virtual inclusion ratio, and a volume of the sample,
   wherein an index evaluating the fracture performance of the machine component is derived by a unit of the virtual cell having the virtual unit volume derived by the virtual unit volume deriving process, and the fracture performance of the machine component is evaluated by using the derived index.

2. The component fracture evaluation method according to claim 1, further comprising:
   an operating stress deriving process deriving a stress amplitude of an operating stress acting on each of the virtual cells when a repetitive load is applied on the machine component with a loading condition set in advance;
   an estimated fatigue strength deriving process deriving a stress amplitude of a fatigue strength by each inclusion size at each virtual cell by substituting respective values into a formula of the fatigue strength represented by the inclusion size, a hardness of the machine component or a strength of a material of the machine component, and a stress ratio of the machine component, being the fatigue strength starting from an inclusion existing in the machine component and as the fatigue strength for a predetermined number of repetitions of a repeatedly applied predetermined load, on the assumption that the distribution function of the inclusion size follows the generalized Pareto distribution having the coefficients derived by the coefficient deriving process;
   a fatigue strength determination function deriving process deriving a fatigue strength determination function indicating whether or not the operating stress exceeds the fatigue strength as for each of the virtual cells based on the fatigue strength derived by the estimated fatigue strength deriving process and the operating stress derived by the operating stress deriving process;
   a virtual cell fatigue strength excess probability deriving process deriving a fatigue strength excess probability being a probability in which the operating stress acting on the virtual cell when a repetitive load is applied on the machine component with a loading condition set in advance exceeds the fatigue strength as for each of the virtual cells based on a density function of the inclusion size having the coefficients derived by the coefficient deriving process, the virtual inclusion ratio, and the fatigue strength determination function;
   a whole fatigue strength excess probability deriving process deriving a fatigue strength excess probability being a probability in which the operating stress acting on the machine component when the repetitive load is applied on the machine component with the loading condition set in advance exceeds the fatigue strength based on the fatigue strength excess probability derived by the virtual cell fatigue strength excess probability deriving process; and
   a whole fatigue strength excess probability output process outputting the fatigue strength excess probability derived by the whole fatigue strength excess probability deriving process.

3. The component fracture evaluation method according to claim 2,
   wherein the inclusion size is a value in which a square root of a cross-sectional area of the inclusion obtained by projecting a shape of the inclusion existing in the sample on a plane is taken, or a value in which a square root of an estimated value of a cross-sectional area of the inclusion obtained from a representative size of a figure is taken when the shape of the inclusion existing in the sample is approximated to the predetermined figure.

4. The component fracture evaluation method according to claim 2,
wherein the operating stress is an amplitude of an equivalent stress at each position of the machine component, or an amplitude of a principal stress in a direction where a variation of the principal stress at each position of the machine component becomes a maximum, and
the stress ratio is a stress ratio of the equivalent stress at each position of the machine component, or a stress ratio of the principal stress in a direction where the variation of the principal stress at each position of the machine component becomes the maximum.

5. The component fracture evaluation method according to claim 2, further comprising:
a sub virtual cell setting process equally dividing at least one of the virtual cells having the virtual unit volume derived by the virtual unit volume deriving process into plural sub virtual cells,
wherein the operating stress deriving process derives the stress amplitude of the operating stress acting on each of the sub virtual cells when the repetitive load is applied on the machine component with the loading condition set in advance as for the virtual cell where the sub virtual cells are set,
the fatigue strength determination function deriving process derives the fatigue strength determination function indicating whether or not the operating stress exceeds the fatigue strength as for each of the sub virtual cells based on the fatigue strength derived by the estimated fatigue strength deriving process and the operating stress derived by the operating stress deriving process as for the virtual cell where the sub virtual cells are set,
the virtual cell fatigue strength excess probability deriving process derives the fatigue strength excess probabilities each being a probability in which the operating stress acting on the sub virtual cell exceeds the fatigue strength when the repetitive load is applied on the machine component with the loading condition set in advance as for the respective sub virtual cells based on the virtual unit volume, the volume of the sub virtual cell, the density function of the inclusion size having the coefficients derived by the coefficient deriving process, the virtual inclusion ratio, and the fatigue strength determination function, and derives one in which these are added up as the fatigue strength excess probability at the virtual cell as for the virtual cell where the sub virtual cells are set.

6. A component fracture evaluation device evaluating fracture performance of a machine component, comprising:
a computer processor; and
a memory storing a program of instructions for:
a threshold value excess number of inclusions deriving unit deriving a threshold value excess number of inclusions, the threshold value excess number of inclusions being the number of inclusions whose inclusion size exceeds a threshold value among the inclusions contained in a sample based on the inclusion size being a size of the inclusion extracted from the sample made up of the same kind of material as a material constituting the machine component;
a coefficient deriving unit deriving coefficients of a generalized Pareto distribution based on the inclusion size of the extracted inclusion, the threshold value excess number of inclusions, and the threshold value on an assumption that a distribution function of the inclusion size of the extracted inclusion follows the generalized Pareto distribution;
a virtual inclusion ratio deriving unit deriving a virtual inclusion ratio being a ratio between the threshold value excess number of inclusions being the number of inclusions whose inclusion size exceeds the threshold value among the inclusions contained in the sample and a zero excess number of inclusions being the number of inclusions whose inclusion size exceeds "0" (zero) among the inclusions contained in the sample; and
a virtual unit volume deriving unit deriving a virtual unit volume being a volume of a virtual cell when the machine component is equally divided by plural virtual cells each containing one inclusion based on the threshold value excess number of inclusions, the virtual inclusion ratio, and a volume of the sample,
wherein an index evaluating the fracture performance of the machine component by a unit of the virtual cell having the virtual unit volume derived by the virtual unit volume deriving unit is derived, and the fracture performance of the machine component is evaluated by using the derived index.

7. The component fracture evaluation device according to claim 6, further comprising:
an operating stress deriving unit deriving a stress amplitude of an operating stress acting on each of the virtual cells when a repetitive load is applied on the machine component with a loading condition set in advance;
an estimated fatigue strength deriving unit deriving a stress amplitude of a fatigue strength by each inclusion size at each virtual cell, by substituting respective values into a formula of the fatigue strength represented by the inclusion size, a hardness of the machine component or a strength of the material of the machine component, and a stress ratio of the machine component, being the fatigue strength starting from the inclusion existing in the machine component and as the fatigue strength for a predetermined number of repetitions of a repeatedly applied predetermined load, on an assumption that a distribution function of the inclusion size follows a generalized Pareto distribution having the coefficients derived by the coefficient deriving unit;
a fatigue strength determination function deriving unit deriving a fatigue strength determination function indicating whether or not the operating stress exceeds the fatigue strength as for each of the virtual cells based on the fatigue strength derived by the estimated fatigue strength deriving unit and the operating stress derived by the operating stress deriving unit;
a virtual cell fatigue strength excess probability deriving unit deriving a fatigue strength excess probability being a probability in which the operating stress acting on the virtual cell when a repetitive load is applied on the machine component with a loading condition set in advance exceeds the fatigue strength as for each of the virtual cells based on a density function of the inclusion size having the coefficients derived by the coefficient deriving unit, the virtual inclusion ratio, and the fatigue strength determination function;
a whole fatigue strength excess probability deriving unit deriving a fatigue strength excess probability being a probability in which the operating stress acting on the machine component when the repetitive load is applied on the machine component with the loading condition set in advance exceeds the fatigue strength based on the fatigue strength excess probability derived by the virtual cell fatigue strength excess probability deriving unit; and a whole fatigue strength excess probability output unit outputting the fatigue strength excess probability derived by the whole fatigue strength excess probability deriving unit.

8. The component fracture evaluation device according to claim 7,
wherein the inclusion size is a value in which a square root of a cross-sectional area of the inclusion obtained by projecting a shape of the inclusion existing in the sample on a plane is taken, or a value in which a square root of an estimated value of a cross-sectional area of the inclusion obtained from a representative size of a figure when the shape of the inclusion existing in the sample is approximated to the predetermined figure is taken.

9. The component fracture evaluation device according to claim 7,
wherein the operating stress is an amplitude of an equivalent stress at each position of the machine component, or an amplitude of a principal stress in a direction where a variation of the principal stress at each position of the machine component becomes a maximum, and
the stress ratio is a stress ratio of the equivalent stress at each position of the machine component, or a stress ratio of the principal stress in a direction where a variation of the principal stress at each position of the machine component becomes the maximum.

10. The component fracture evaluation device according to claim 7, further comprising:
a sub virtual cell setting unit equally dividing at least one of the virtual cells having the virtual unit volume derived by the virtual unit volume deriving unit into plural sub virtual cells,
wherein the operating stress deriving unit derives the stress amplitude of the operating stress acting on each of the sub virtual cells when the repetitive load is applied on the machine component with the loading condition set in advance as for the virtual cell where the sub virtual cells are set,
the fatigue strength determination function deriving unit derives the fatigue strength determination function indicating whether or not the operating stress exceeds the fatigue strength as for each of the sub virtual cells based on the fatigue strength derived by the estimated fatigue strength deriving unit and the operating stress derived by the operating stress deriving unit as for the virtual cell where the sub virtual cells are set,
the virtual cell fatigue strength excess probability deriving unit derives the fatigue strength excess probabilities each being a probability in which the operating stress acting on the sub virtual cell exceeds the fatigue strength when the repetitive load is applied on the machine component with the loading condition set in advance as for the respective sub virtual cells based on the virtual unit volume, a volume of the sub virtual cell, the density function of the inclusion size having the coefficients derived by the coefficient deriving unit, the virtual inclusion ratio, and the fatigue strength determination function, and derives one in which these are added up as the fatigue strength excess probability at the virtual cell as for the virtual cell where the sub virtual cells are set.

11. A non-transitory computer readable medium storing a program of instructions for causing a computer to execute an evaluation of fracture performance of a machine component, the computer program causing the computer to execute:
a threshold value excess number of inclusions deriving process deriving a threshold value excess number of inclusions being the number of inclusions whose inclusion size exceeds a threshold value among the inclusions contained in a sample based on the inclusion size being a size of the inclusion extracted from the sample made up of the same kind of material as a material constituting the machine component;
a coefficient deriving process deriving coefficients of a generalized Pareto distribution based on the inclusion size of the extracted inclusion, the threshold value excess number of inclusions, and the threshold value on an assumption that a distribution function of the inclusion size of the extracted inclusion follows the generalized Pareto distribution;
a virtual inclusion ratio deriving process deriving a virtual inclusion ratio being a ratio between the threshold value excess number of inclusions being the number of inclusions whose inclusion size exceeds the threshold value among the inclusions contained in the sample and a zero excess number of inclusions being the number of inclusions whose inclusion size exceeds "0" (zero) among the inclusions contained in the sample; and
a virtual unit volume deriving process deriving a virtual unit volume being a volume of a virtual cell when the machine component is equally divided by plural virtual cells each containing one inclusion based on the threshold value excess number of inclusions, the virtual inclusion ratio, and a volume of the sample,
wherein an index evaluating the fracture performance of the machine component by a unit of the virtual cell having the virtual unit volume derived by the virtual unit volume deriving process is derived, and the fracture performance of the machine component is evaluated by using the derived index.

* * * * *